US012599603B2

(12) United States Patent
Li et al.

(10) Patent No.: US 12,599,603 B2
(45) Date of Patent: Apr. 14, 2026

(54) METHODS OF TREATMENT

(71) Applicant: INTRA-CELLULAR THERAPIES, INC., New York, NY (US)

(72) Inventors: Peng Li, New Milford, NJ (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 973 days.

(21) Appl. No.: 17/640,050

(22) PCT Filed: Sep. 3, 2020

(86) PCT No.: PCT/US2020/049248

§ 371 (c)(1), (2) Date: Mar. 3, 2022

(87) PCT Pub. No.: WO2021/046250

PCT Pub. Date: Mar. 11, 2021

(65) Prior Publication Data

US 2022/0354851 A1 Nov. 10, 2022

Related U.S. Application Data

(60) Provisional application No. 62/895,476, filed on Sep. 3, 2019.

(51) Int. Cl.

*A61K 31/519* (2006.01)
*A61K 31/505* (2006.01)
*A61K 38/00* (2006.01)
*A61P 35/00* (2006.01)

(52) U.S. Cl.

CPC .......... *A61K 31/519* (2013.01); *A61K 31/505* (2013.01); *A61K 38/005* (2013.01); *A61P 35/00* (2018.01)

(58) Field of Classification Search

CPC .. A61K 31/519; A61K 31/505; A61K 38/005; A61P 35/00

See application file for complete search history.

(56) References Cited

U.S. PATENT DOCUMENTS

| | | | | |
|---|---|---|---|---|
| 4,690,935 | A | 9/1987 | Taylor et al. | |
| 8,273,751 | B2 | 9/2012 | Li | |
| 8,633,180 | B2 * | 1/2014 | Li | A61P 25/30 544/247 |
| 8,664,207 | B2 | 3/2014 | Li et al. | |
| 9,073,936 | B2 | 7/2015 | Li et al. | |
| 9,545,406 | B2 | 1/2017 | Wennogle | |
| 9,708,294 | B2 | 7/2017 | Li et al. | |
| 9,884,872 | B2 | 2/2018 | Li | |
| 10,092,575 | B2 | 10/2018 | Branstetter et al. | |
| 10,150,774 | B2 | 12/2018 | Li et al. | |
| 10,682,355 | B2 | 6/2020 | Wennogle | |
| 10,849,862 | B2 * | 12/2020 | Kawakami | C07K 16/30 |
| 11,291,666 | B2 | 4/2022 | Snyder et al. | |
| 11,504,372 | B2 | 11/2022 | Wennogle | |
| 2014/0128353 | A1 | 5/2014 | Bannister et al. | |
| 2014/0235556 | A1 | 8/2014 | Halse et al. | |
| 2015/0017267 | A1 | 1/2015 | Guedes et al. | |
| 2016/0324860 | A1 | 11/2016 | Hendrick et al. | |
| 2016/0362489 | A1 | 12/2016 | Yang | |
| 2020/0085782 | A1 | 3/2020 | Gallatin et al. | |
| 2020/0405879 | A1 | 12/2020 | Feingold et al. | |
| 2021/0338679 | A1 | 11/2021 | Li et al. | |
| 2022/0354851 | A1 | 11/2022 | Li et al. | |

FOREIGN PATENT DOCUMENTS

| | | | |
|---|---|---|---|
| WO | 2006/133261 | A2 | 12/2006 |
| WO | 2016/022893 | A1 | 2/2016 |
| WO | 2017/011831 | A1 | 1/2017 |
| WO | WO 2018/093591 | A1 | 5/2018 |
| WO | WO 2019/046778 | | 3/2019 |
| WO | WO 2020/146384 | | 7/2020 |
| WO | 2023/173131 | A2 | 9/2023 |

OTHER PUBLICATIONS

Pantziarka, Pan, Vidula Sukhatme, Sergio Crispino, Gauthier Bouche, Lydie Meheus, and Vikas P. Sukhatme. "Repurposing drugs in oncology (ReDO) selective PDE5 inhibitors as anti-cancer agents." ecancermedicalscience 12 (2018) (Year: 2018).*

Yue, Grace Gar-Lee, Hin-Fai Kwok, Julia Kin-Ming Lee, Lei Jiang, Eric Chun-Wai Wong, Si Gao, Hing-Lok Wong et al. "Combined therapy using bevacizumab and turmeric ethanolic extract (with absorbable curcumin) exhibited beneficial efficacy in colon cancer mice." Pharmacological Research 111 (2016): 43-5 (Year: 2016).*

Peng, Ting, Jun Gong, Yongzhe Jin, Yanping Zhou, Rongsheng Tong, Xin Wei, Lan Bai, and Jianyou Shi. "Inhibitors of phosphodiesterase as cancer therapeutics." European journal of medicinal chemistry 150 (2018): 742-756) (Year: 2018).*

Fajardo, Alexandra M., Gary A. Piazza, and Heather N. Tinsley. "The role of cyclic nucleotide signaling pathways in cancer: targets for prevention and treatment." Cancers 6, No. 1 (2014): 436-458 (Year: 2014).*

Swart, Maarten, Inge Verbrugge, and Joost B. Beltman. "Combination approaches with immune-checkpoint blockade in cancer therapy." Frontiers in oncology 6 (2016): 233 (Year: 2016).*

Abusnina et al., "Anti-proliferative Effect of Curcumin on Melanoma Cells is Mediated by PDEIA Inhibition that Regulates the Epigenetic Integrator UHRFI," *Mol. Nutr. Food Res.*, vol. 55, DD. 1677-1689, (2011).

(Continued)

*Primary Examiner* — James H Alstrum-Acevedo
*Assistant Examiner* — Carolyn L. Ladd
(74) *Attorney, Agent, or Firm* — Hoxie & Associates LLC

(57) ABSTRACT

The disclosure relates to the combination of inhibitors of phosphodiesterase 1 (PDE1) useful for the treatment of certain cancers or tumors, such as colon cancer. In another embodiment, the disclosure relates to the use of inhibitors of PDE1 and an optional antitumor agent for the treatment of certain cancers or tumors.

12 Claims, 2 Drawing Sheets

(56) References Cited

OTHER PUBLICATIONS

Ahlstrom, et al., "Cyclic nucleotide phosphodiesterases (PDEs) in human osteoblastic cells; the effect of PDE inhibition on cAMP accumulation", *Cell Mol Biol Lett,* 10:305-319, (2005).
Ahmad, et al., "Cyclic Nucleotide Phosphodiesterases: important signaling modulators and therapeutic targets", *Oral Diseases,* 21(1), pp. e25-e50, (2015).
Almahariq et al., "Pharmacological Inhibition and Genetic Knockdown of Exchange Protein Directly Activated by CAMP 1 Reduce Pancreatic Cancer Metastasis In Vivo," *Molecular Pharmacology,* vol. 87, No. 2, pp. 142-149, (2015).
Argyle et al., "Targeting Macrophage-Recruiting Chemokines as a Novel Therapeutic Strategy to Prevent the Progression of Solid Tumors," *Frontiers in Immunology,* vol. 9, 15 pages, (2018).
Boyd et al., "cAMP-Phosphodiesterase PDE4D as a Target for Colon Cancer Therapy," *The FASEB Journal,* vol. 31, No. 1, 2 pages, (2017).
Brodbelt et al., "Glioblastoma in England: 2007-2011", *Eur. J. Cancer,* vol. 51, pp. 533-542, (2015).
Chen et al., "cAMP Inhibits Cell Migration by Interfering with Rae-induced Lamellipodium Formation," *Journal of Biological Chemistry,* vol. 283, No. 20, pp. 13799-13805, (2008).
Coussens et al., "Inflammation and Cancer," *Nature,* vol. 420, No. 6917, pp. 860-867, (2002).
Daniel et al., "Sensitivity of GBM Cells to CAMP Agonist-mediated Apoptosis Correlates with CD44 Expression and Agonist Resistance with MAPK Signaling," *Cell Death and Disease,* vol. 7, No. e2494, 11 pages, (2016).
Insel et al., "Cyclic AMP is Both a Pro-apoptotic and Anti-apoptotic Second Messenger," *Acta Physiol* (*Oxf*), vol. 204, No. 2, pp. 277-287, (2012).
Jang, et al., "Adaptation of cAMP signaling system in SH-SY5Y neuroblastoma cells following expression of a constitutively active stimulatory G protein alpha, Q227L Gsalpha", *Exp Mol Med,* 33:37-45, (2001).
Jiang et al., "Expression and Regulation of mRNA for Distinct Isoforms of cAMP-Specific PDE-4 in Mitogen-Stimulated and Leukemic Human Lymphocytes," *Cell Biochem Biophys,* vol. 28, pp. 135-160, (1998).
Kim et al., "Antiinflammatory cAMP Signaling and Cell Migration Genes Co-opted by the Anthrax Bacillus," *PNAS*, vol. 105, No. 16, pp. 6150-6155, (2008).
Marko et al., "Cyclic 3' ,5'-nucleotide Phosphodiesterases: Potential Targets for Anticancer Therapy," *Chem Res Toxicol,* vol. 13, pp. 944-948, (2000).
Medina, A, "Therapeutic Utility of Phosphodiesterase Type I Inhibitors in Neurological Conditions," *Frontiers in Neuroscience,* vol. 5, No. 21, pp. 1-5, (2011).
Pantziarka, et al., "Repurposing drugs in oncology (ReDO)-selective PDE5 inhibitors as anti-cancer agents", *ecancermedicalscience,* 12, pp. 1-22, (2018).
Peng et al., "Inhibitors of Phosphodiesterase as Cancer Therapeutics," European *Journal of Medicinal Chemistry,* vol. 150, pp. 742-756, (2018).
Rowther et al., "Cyclic Nucleotide Phosphodiesterase-IC (PDEIC) Drives Cell Proliferation Migration and Invasion in Glioblastoma Multiforme Cells In Vitro," *Molecular Carcinogenesis,* vol. 55, pp. 268-279, (2016).
Rybalkin, et al., "Calmodulin-stimulated cyclic nucleotide phosphodiesterase (PDEIC) is induced in human arterial smooth muscle cells of the synthetic, proliferative phenotype", *J Clin Invest,* 100:2611-2621, (1997).
Savai et al., "Targeting Cancer with Phosphodiesterase Inhibitors," *Expert Opin. Investig. Drugs,* vol. 19, No. 1, pp. 117-131, (2010).
Shimizu et al., "Characterization of Phosphodiesterase 1 in Human Malignant Melanoma Cell Lines," *AntiCancer Research,* vol. 29, pp. 1119-1122, (2009).
Shiri et al., "Dendrosomal Curcumin Suppresses Metastatic Breast Cancer in Mice by Changing MI/M2 Macrophage Balance in the Tumor Microenvironment," *Asian Pac J Cancer Prev.,* vol. 16, No. 9, pp. 3917-3922, (2015).
Soon, L, "A Discourse on Cancer Cell Chemotaxis: Where to From Here?", *IUBMB Life,* vol. 59, No. 2, pp. 60-67, (2007).
Stupp et al., "Radiotherapy Plus Concomitant and Adjuvant Temozolomide for Glioblastoma", *N Engl J Med,* vol. 352, No. 10, pp. 987-996, (2005).
Touat et al., "Glioblastoma Targeted Therapy: Updated Approaches from Recent Biological Insights," *Ann. Oncol.,* vol. 28, No. 7, pp. 1457-1472, (2017).
Vitale et al., "A New Therapeutic Strategy Against Cancer: CAMP Elevating Drugs and Leptin," *Cancer Biology & Therapy,* vol. 8, No. 12, pp. 1191-1193, (2009).
Watanabe, et al., "Phosphodiesterase 4 regulates the migration of B 16-FIO melanoma cells" *Exp Ther Med,* 4:205-210, (2012).
"Gene expression," Wikipedia, 17 pages, (2017); accessed on Jul. 18, 2019 at https :/ /en. wikipedia.org/w /index. php ?title=Gene_expression&oldid=803 7185 22.
Zong et al., "The Cellular Origin for Malignant Glioma and Prospects for Clinical Advancements," *Expert Rev Mol Diagn.,* vol. 12, No. 4, pp. 383-394, (2012).
Hayakawa, et al., "Enhanced anti-tumor effects of the PD-1/PD-LI blockade by combining a highly absorptive form of NF-KB/STAT3 inhibitor curcumin", *J. Immunother. Cancer,* 2(Suppl 3), P210, (2014).
Johnson, et al., "Curcumin for chemoprevention of colon cancer", *Cancer Letters,* 255(2), pp. 170-181, (2007).
Abusnina et al., "Anti-proliferative effect of curcumin on melanomacells is mediated by PDE1A inhibition that regulates the epigenetic integrator UHRF1," *Mol. Nutr. Food Res.,* 55(11): 1677-1689, (2011).
Barakat et al., "Substituted spirooxindole derivatives as potent anticancer agents through inhibition of phosphodiesterase 1," *RSC Advances,* 8(26):14335-14346, (2018).
Dou et al., "Curcumin Suppresses the Colon Cancer Proliferation by Inhibiting Wnt/β-Catenin Pathways via miR-130a," *Frontiers in Pharmacology,* 8(877), (2017).
Tong et al., "Curcumin suppresses colon cancer cell invasion via AMPK-induced inhibition of NF-κB, uPA activator and MMP9," *Oncology Letters,* 12(5):4139-4146, (2016).
Levy, I. et al., "Phosphodiesterase Function and Endocrine Cells: Links to Human Disease and Roles in Tumor Development and Treatment," Current Opinion in Pharmacology, vol. 11, pp. 689-697, (2011).
Li, P. et al., "Discovery of Potent and Selective Inhibitors of Phosphodiesterase 1 for the Treatment of Cognitive Impairment Associated with Neurodegenerative and Neuropsychiatric Diseases," Journal of Medicinal Chemistry, vol. 59, No. 3, pp. 1149-1164, (2016).
Martinez, F. et al., "Genetic Programs Expressed in Resting and IL-4 Alternatively Activated Mouse and Human Macrophages: Similarities and Differences," Blood, vol. 121, No. 9, 13 pages, (2013).
Mietto, B. et al., "Role of IL-10 in Resolution of Inflammation and Functional Recovery after Peripheral Nerve Injury," The Journal of Neuroscience, vol. 35, No. 50, pp. 16431-16442, (2015).
Snyder, G. et al., "Suppression of CNS Inflammation by Phosphodiesterase-1 (PDE1) Inhibitors: Toward New Treatments for Neurodegenerative Diseases," Database Embase, Database Accession No. EMB-620612543, Alzheimer's Association International Conference AAIC 2017 in London, 2 pages, Abstract only.
Zhao, A. et al., "Recent Advances in the Study of Ca2+/CaM-activated Phosphodiesterases: Expression and Physiological Functions," Adv Second Messenger Phosphoprotein Res, vol. 31, pp. 237-251, (1997).

* cited by examiner

METHODS OF TREATMENT

CROSS-REFERENCE TO RELATED APPLICATIONS

This application is a U.S. National Stage application under 35 U.S.C. § 371 of International Application No. PCT/US2020/049248, filed on Sep. 3, 2020, which claims priority to and the benefit of U.S. Provisional Application No. 62/895,476, filed on Sep. 3, 2019, the contents of each of which are hereby incorporated by reference in their entireties.

FIELD OF DISCLOSURE

The field relates to inhibitors of phosphodiesterase 1 (PDE1) useful for the treatment of certain cancers and tumors, such as colon cancer. The field further relates to the administration of inhibitors of phosphodiesterase 1 (PDE1) for the for the treatment of certain cancers and tumors, such as colon cancer.

BACKGROUND OF THE DISCLOSURE

Colorectal cancer is the third most commonly diagnosed cancer in men and the second in women worldwide, and accounts for an estimated 50,000 deaths per year. In contrast to incidence trends, decreasing colorectal cancer mortality rates have been observed in a large number of countries and are most likely attributed to colorectal cancer screening, reduced prevalence of risk factors, and/or improved therapies. However, when widespread malignancy is encountered, these cases are not responsive to curative treatments.

It is additionally estimated that metastases cause 90% of cancer-related deaths worldwide. In most cases, the metastatic tumour cells develop methods to evade immune responses and become resistant to therapy. Resistance to cancer treatment can be intrinsic to the tumour cells, but it is often conferred or augmented by non-malignant cells that make up the tumour microenvironment (TME). The TME is composed of tissue-resident cells, stromal cells, and other cells recruited by the tumor, and so it may include endothelial cells, pericytes, fibroblasts, mesenchymal stem cells, and a variety of immune cells, including regulatory T (Treg) cells, mast cells, neutrophils, myeloid-derived suppressor cells, and tumor associated macrophages. These cells promote tumor angiogenesis, cancer cell invasion, and/or disrupt immune surveillance. Macrophages are among the most common type of tumor-associated cells. Researchers originally assumed that these immune cells were part of the body's response to reject tumours, and indeed a major check on the development of cancers is the immune system's surveillance and reaction to the presence of cancer, by cells of the innate immune system (e.g., macrophage, neutrophils) as well as cells associated with an adaptive immune response (e.g., T and B cells).

However, in some cases, the cancer is able to evade and co-opt the immune system, so that rather than attacking the tumor, these immune system cells become part of the tumor's support and defense system. The immune TME can be modified to support the tumour and promote its progression while suppressing immune cell-mediated cytotoxicity. Substantial clinical and experimental evidence indicates that macrophages—present abundantly in most tumour types—have a major regulatory role in promoting tumour progression to malignancy. Macrophages in both primary tumors (tumor-associated macrophages or TAMs) and in metastatic tumors (metastasis-associated macrophages or MAMs) are abundant in most solid tumors and phosphodiesterase's may be associated with tumor metastasis. Accumulation of TAMs, MAMs, and their progenitor cells is seemingly driven by chemokine ligands released by tumor and stromal cells. For example, there is evidence that TAMs and MAMs are derived at least in part from CCR2-expressing monocytes recruited by CCL2-expressing tumor cells and/or CCL2-expressing stromal cells. The precise mechanisms are not fully defined, however, and other CCR2 ligands such as CCL12, cytokines such as VEGF and CSF1, and other chemoattractant signals such as CCL5-CCR5, CCL20-CCR6, CXCL12-CXCR4 may provide an alternative or additional chemoattractant pathway for recruitment of TAMs. Thus, efforts to target specific chemoattractant receptors or ligands, e.g., specifically blocking the CCR2-CCL2 interaction, have not been entirely effective, probably because the cancers are capable of exploiting alternative pathways.

Eleven families of phosphodiesterases (PDEs) have been identified but only PDEs in Family I, the Ca2+/calmodulin-dependent phosphodiesterases (CaM-PDEs), which are activated by Ca2+/calmodulin and have been shown to mediate the calcium and cyclic nucleotide (e.g. cGMP and cAMP) signaling pathways. The three known CaM-PDE genes, PDE1A, PDE1B, and PDE1C, are all expressed in central nervous system tissue. PDE1A is expressed in the brain, lung and heart. PDE1B is primarily expressed in the central nervous system, but it is also detected in monocytes and neutrophils and has been shown to be involved in inflammatory responses of these cells. PDE1C is expressed in olfactory epithelium, cerebellar granule cells, striatum, heart, and vascular smooth muscle. PDE1C has been demonstrated to be a major regulator of smooth muscle proliferation in human smooth muscle.

Cyclic nucleotide phosphodiesterases down-regulate intracellular cAMP and cGMP signaling by hydrolyzing these cyclic nucleotides to their respective 5'-monophosphates (5'AMP and 5'GMP), which are inactive in terms of intra-cellular signaling pathways. Both cAMP and cGMP are central intracellular second-messengers and they play roles in regulating numerous cellular functions. PDE1A and PDE1B preferentially hydrolyze cGMP over cAMP, while PDE1C shows approximately equal cGMP and cAMP hydrolysis.

With respect to PDE1C in particular, recent evidences indicate that PDE1C is a proliferation associated gene, since it is expressed exclusively in proliferating vascular smooth muscle cells. (Rybalkin S D, et al., Calmodulin-stimulated cyclic nucleotide phosphodiesterase (PDE1C) is induced in human arterial smooth muscle cells of the synthetic, proliferative phenotype. J Clin Invest 1997; 100:2611-2621.) In addition, there have been sporadic reports of PDE1C expression along with other PDE subtypes in experimental tumor models such as melanoma (Watanabe Y, et al., Phosphodiesterase 4 regulates the migration of B16-F10 melanoma cells. Exp Ther Med 2012; 4:205-210.), neuroblastoma (Jang I S, Juhnn Y S. Adaptation of cAMP signaling system in SH-SY5Y neuroblastoma cells following expression of a constitutively active stimulatory G protein alpha, Q227L Gsalpha. Exp Mol Med 2001; 33:37-45), and osteosarcoma (Ahlström M, et al., Cyclic nucleotide phosphodiesterases (PDEs) in human osteoblastic cells; the effect of PDE inhibition on cAMP accumulation. Cell Mol Biol Lett 2005; 10:305-319).

Tumor-promoting cellular proliferation, migration, tissue invasion and inflammation are considered enabling characteristics of cancer development. Each of these processes are time-dependent, variable and complex involving a multitude of signal transduction pathways. It is believed that multi-targeted agents produce greater benefits than those observed with single-targeted therapies, have acceptable tolerability profiles, and are active against a broader range of tumor types. Regulation of cyclic nucleotide signaling is properly regarded as a composite of multiple component pathways involved in diverse aspects of tumor cell function. The impairment of cAMP generation has been described in various cancer pathologies. Attempts to directly regulate cyclic nucleotides in cancer cells, while being antiproliferative have not been productive, owing to high cytotoxicity. New, safer and selective strategies for modulating cAMP in cancer cells are needed.

SUMMARY OF THE DISCLOSURE

The inventors have previously shown that inhibition of PDE1 activity using the presently disclosed compounds can safely restore cAMP function in a wide spectrum of pathological conditions, including models of neurodegeneration and neuroinflammation, heart failure, pulmonary hypertension and peripheral inflammation and in humans with certain diseases. More recently, the inventors have shown that PDE1 inhibitors obstruct cellular migration of microglia and monocytes. Recent evidence indicates that PDE1, particularly the PDE1C isoform, is over expressed in experimental tumor models such as melanoma, neuroblastoma, and osteosarcoma. In addition, focal genomic over representation of PDE1C in Glioblastoma Multiforme (GBM) cells has been demonstrated. Genomic gain of PDE1C is associated with increased expression in GBM-derived cell cultures and is essential for driving cell proliferation, migration and invasion in cancer cells.

Many types of cancer cells over express PDE1 activity, which is identified through various biomarkers, such as increased RNA expression, DNA copy number, PDE1 binding (PET or radio-isotope retention of PDE1 inhibitor molecules) or enzymatic activity. These cancer cells also exhibit low levels of cAMP, which can be increased by PDE1 inhibitors. Such characteristics can be treated with PDE-1 inhibitors alone or in combination with chemotherapeutics, gene therapeutics and/or immunologic approaches. Inhibiting PDE1 provokes apoptotic cell death, prevents migration, limits metastasis, and reduces inflammation. In this way, PDE1 inhibitors are synergistic with chemotherapeutics and immunologic approaches.

Without being bound by theory, it is believed that inhibition of selective PDE1 isoforms, which raises the levels of intracellular cAMP (and/or cGMP), induces apoptosis and cell cycle arrest in a broad spectrum of tumor cells and regulates the tumor microenvironment preventing cellular migration, inflammation, and tissue invasion. Therefore, the development and clinical application of inhibitors specific for individual PDE1 and its isoforms, particularly PDE1C, may selectively restore normal intracellular signaling, providing antitumor therapy with reduced adverse effects. Without being bound by theory, it is further believed that the PDE1 inhibitors of the present disclosure inhibit recruitment of immune system cells, including macrophages, and other cells to the cancer, and to inhibit the metastasis, tumor angiogenesis, cancer cell invasion, and disruption of immune surveillance provided by the recruited cells. PDE1 inhibits not only CCL2 but also other cytokines and chemokines believed to be involved in this recruitment and is therefore expected to be more effective than therapies such as monoclonal antibodies or other specific inhibitors of the CCR2-CCL2 interaction.

The disclosure also provides the use of a PDE1 inhibitor for the treatment of a cancer or tumor, including, e.g., carcinomas, melanomas, and astrocytomas. Moreover, impaired cAMP (or cGMP) levels may arise from overexpression of PDE1 isoforms in various cancer pathologies. Inhibition of selective PDE1 isoforms, which raises the levels of intracellular cAMP (and/or cGMP), induces apoptosis and cell cycle arrest in a broad spectrum of tumor cells and regulates the tumor microenvironment preventing cellular migration, inflammation, and tissue invasion. Therefore, the development and clinical application of inhibitors specific for individual PDE1 may selectively restore normal intracellular signaling, providing antitumor therapy with reduced adverse effects.

Previous studies have demonstrated that PDE1 (i.e., PDE1C) is significantly overexpressed in the tumor environment of glioblastoma patients compared to healthy patients (i.e., those not suffering from glioblastoma). siRNA mediated silencing of PDE1C has been shown to inhibit proliferation and invasion in patient-derived cell cultures of glioblastoma. Without being bound by any theory, inhibition of PDE1 may be effective in the therapeutic intervention of certain cancers or tumors, such as glioblastoma.

In various embodiments, the present application provides for a method of treating colon cancer (e.g., colorectal cancer) comprising administering a pharmaceutically acceptable amount of a PDE1 inhibitor to a subject in need thereof. In some embodiments, the PDE1 inhibitor is administered in combination with an antitumor agent.

In various embodiments, the present disclosure also provides for pharmaceutical compositions comprising Compounds of the present disclosure prepared using conventional diluents or excipients and techniques known in the art. Thus, oral dosage forms may include tablets, capsules, solutions, suspensions and the like.

In various embodiments, the present disclosure also provides PDE1 inhibitors according to Formula I, Ia, II, III, IV, V, VI and/or VII described hereinbelow in free or salt form for use in the treatment of a condition selected from a cancer or tumor, inhibiting the proliferation, migration and/or invasion of tumorous cells, or treating colon cancer, e.g., colorectal cancer.

DETAILED DESCRIPTION OF THE DISCLOSURE

Figure 1:
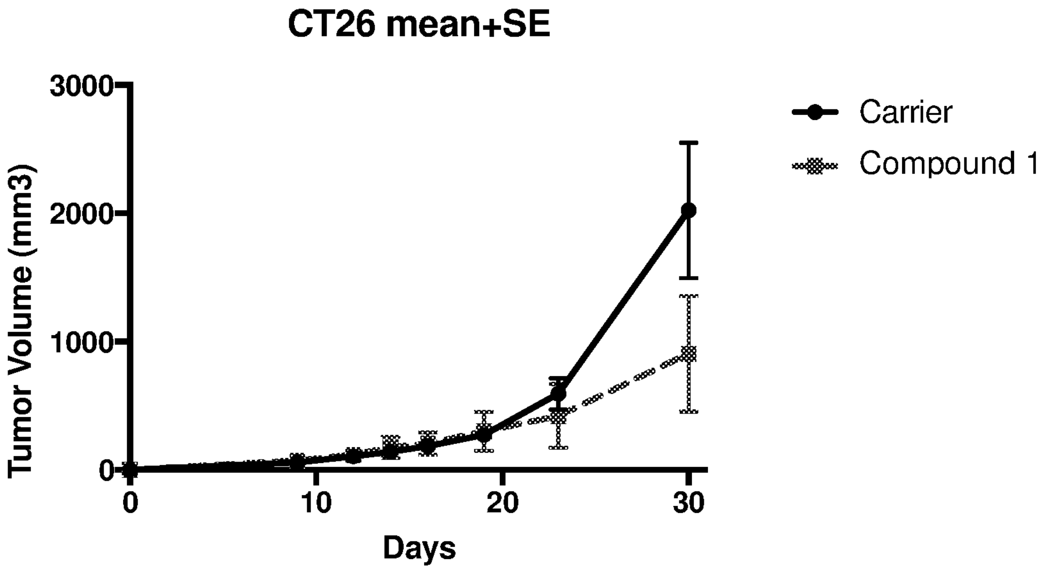
FIG. 1 shows the effect of PDE1 inhibition on CT26 murine cancer cells in samples treated with Compound 1 and untreated control.

Compounds for Use in the Methods of the Disclosure

In one embodiment, the PDE1 inhibitors for use in the methods of treatment and prophylaxis described herein are selective PDE1 inhibitors.

PDE1 Inhibitors

In one embodiment the invention provides that the PDE1 inhibitors for use in the methods of treatment and prophylaxis described herein are compounds of Formula I:

Formula I

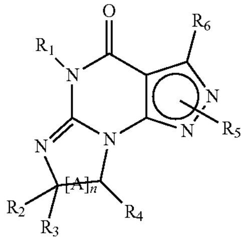

wherein (i) $R_1$ is H or $C_{1-4}$ alkyl (e.g., methyl);

(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(iii) $R_5$ is a substituted heteroarylalkyl, e.g., substituted with haloalkyl; or $R_5$ is attached to one of the nitrogens on the pyrazolo portion of Formula I and is a moiety of Formula A Formula A

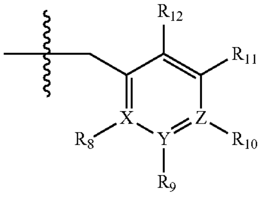

wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl) optionally substituted with halogen, or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1;

(vi) when n=1, A is —$C(R_{13}R_{14})$— wherein $R_{13}$ and $R_{14}$, are, independently, H or $C_{1-4}$ alkyl, aryl, heteroaryl, (optionally hetero)arylalkoxy or (optionally hetero)arylalkyl;

in free, salt or prodrug form, including its enantiomers, diastereoisomers and racemates.

In another embodiment the invention provides that the PDE1 inhibitors for use in the methods as described herein are Formula 1a:

Formula Ia

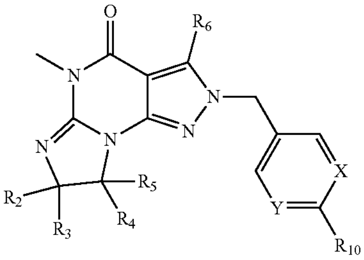

wherein (i) $R_2$ and $R_5$ are independently H or hydroxy and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ and $R_5$ are each H; or $R_2$, $R_4$ and $R_5$ are H and $R_3$ is isopropyl [pref. the carbon carrying $R_3$ having the R configuration];

(ii) $R_6$ is (optionally halo-substituted) phenylamino, (optionally halo-substituted) benzylamino, $C_{1-4}$alkyl, or $C_{1-4}$alkyl sulfide; for example, phenylamino or 4-fluorophenylamino;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl (for example 6-fluoropyrid-2-yl), or thiadiazolyl (e.g., 1,2,3-thiadiazol-4-yl); and X and Y are independently C or N, in free, pharmaceutically acceptable salt or prodrug form, including its enantiomers, diastereoisomers and racemates.

In another embodiment the invention provides that the PDE1 inhibitors for use in the methods of treatment and prophylaxis described herein are compounds of Formula II:

Formula II

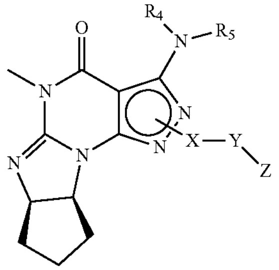

(i) X is $C_{1-6}$alkylene (e.g., methylene, ethylene or prop-2-yn-1-ylene);

(ii) Y is a single bond, alkynylene (e.g., —C≡C—), arylene (e.g., phenylene) or heteroarylene (e.g., pyridylene);

(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R^1$, —$N(R^2)(R^3)$, or $C_{3-7}$cycloalkyl optionally containing at least one atom selected from a group consisting of N or O (e.g., cyclopentyl, cyclohexyl, tetrahydro-2H-pyran-4-yl, or morpholinyl);

(iv) $R^1$ is $C_{1-6}$alkyl, halo$C_{1-6}$alkyl, —OH or —O$C_{1-6}$alkyl (e.g., —$OCH_3$);

(v) $R^2$ and $R^3$ are independently H or $C_{1-6}$alkyl;

(vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;

wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form.

In yet another embodiment the invention provides that the PDE1 inhibitors for use in the methods of treatment and prophylaxis described herein are Formula III:

Formula III

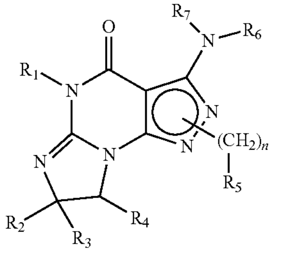

wherein (i) R1 is H or $C_{1-4}$ alkyl (e.g., methyl or ethyl);

(ii) $R_2$ and $R_3$ are independently H or $C_{1-6}$ alkyl (e.g., methyl or ethyl);

(iii) $R_4$ is H or $C_{1-4}$ alkyl (e.g., methyl or ethyl);

(iv) $R_5$ is aryl (e.g., phenyl) optionally substituted with one or more groups independently selected from —C(═O)—$C_{1-6}$ alkyl (e.g., —C(═O)—$CH_3$) and $C_{1-6}$-hydroxyalkyl (e.g., 1-hydroxyethyl);

(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and (vi) n is 1, 2, 3, or 4, in free or salt form.

In yet another embodiment the invention provides that the PDE1 inhibitors for use in the methods of treatment and prophylaxis described herein are Formula IV Formula IV

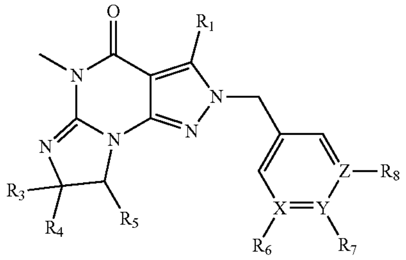

in free or salt form, wherein (i) $R_1$ is $C_{1-4}$alkyl (e.g., methyl or ethyl), or —NH($R_2$), wherein $R_2$ is phenyl optionally substituted with halo (e.g., fluoro), for example, 4-fluorophenyl;

(ii) X, Y and Z are, independently, N or C;

(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively), (iv) $R_6$, $R_7$ and $R_8$ are independently:

H, $C_{1-4}$alkyl (e.g., methyl), pyrid-2-yl substituted with hydroxy, or

—$S(O)_2$—$NH_2$;

(v) Provided that when X, Y and/or Z are N, then $R_6$, $R_7$ and/or $R_8$, respectively, are not present; and when X, Y and Z are all C, then at least one of $R_6$, $R_7$ or $R_8$ is —$S(O)_2$—$NH_2$ or pyrid-2-yl substituted with hydroxy.

In another embodiment the present disclosure provides that the PDE1 inhibitors for use in the methods as described herein are Formula V:

Formula V

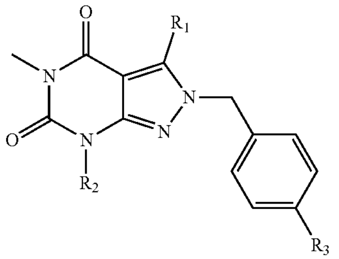

wherein (i) $R_1$ is —NH($R_4$), wherein $R_4$ is phenyl optionally substituted with halo (e.g., fluoro), for example, 4-fluorophenyl;

(ii) $R_2$ is H or $C_{1-6}$alkyl (e.g., methyl, isobutyl or neopentyl);

(iii) $R_3$ is —$SO_2NH_2$ or —COOH;

in free, pharmaceutically acceptable salt or prodrug form, including its enantiomers, diastereoisomers and racemates.

In another embodiment the present disclosure provides that the PDE1 inhibitors for use in the methods as described herein are Formula VI:

Formula VI

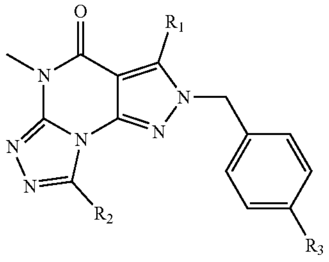

wherein (i) $R_1$ is —NH($R_4$), wherein $R_4$ is phenyl optionally substituted with halo (e.g., fluoro), for example, 4-fluorophenyl;

(ii) $R_2$ is H or $C_{1-6}$alkyl (e.g., methyl or ethyl);

(iii) $R_3$ is H, halogen (e.g., bromo), $C_{1-6}$alkyl (e.g., methyl), aryl optionally substituted with halogen (e.g., 4-fluorophenyl), heteroaryl optionally substituted with halogen (e.g., 6-fluoropyrid-2-yl or pyrid-2-yl), or acyl (e.g., acetyl), in free, pharmaceutically acceptable salt or prodrug form, including its enantiomers, diastereoisomers and racemates.

In another embodiment the present disclosure provides that the PDE1 inhibitors for use in the methods as described herein are Formula VII:

Formula VII

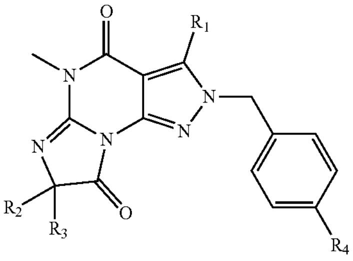

(i) $R_1$ is —NH($R_5$), wherein $R_5$ is phenyl optionally substituted with halo (e.g., fluoro), for example, 4-fluorophenyl;

(ii) $R_2$ and $R_3$ are each independently H or $C_{1-6}$alkyl (e.g., methyl or ethyl);

(iii) $R_4$ is aryl optionally substituted with halogen (e.g., 4-fluorophenyl) or heteroaryl optionally substituted with halogen (e.g., 6-fluoropyrid-2-yl), in free, pharmaceutically acceptable salt or prodrug form, including its enantiomers, diastereoisomers and racemates.

In one embodiment, the present disclosure provides for administration of a PDE1 inhibitor for use in the methods described herein (e.g., a compound according to Formulas I, Ia, II, III, IV, V, VI and/or VII), wherein the inhibitor is a compound according to the following:

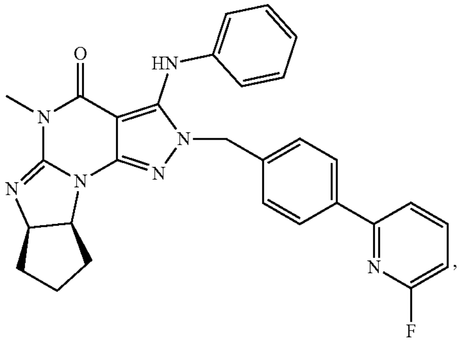

,

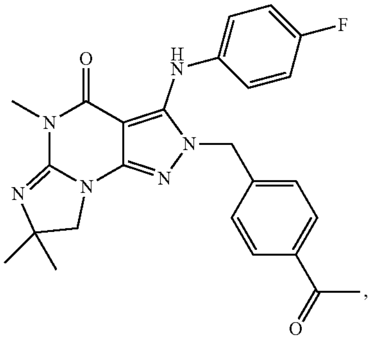

,

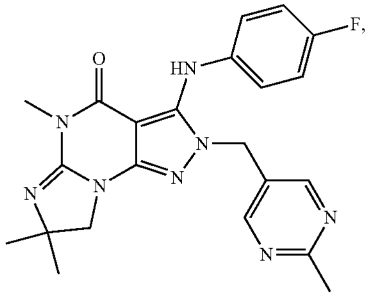

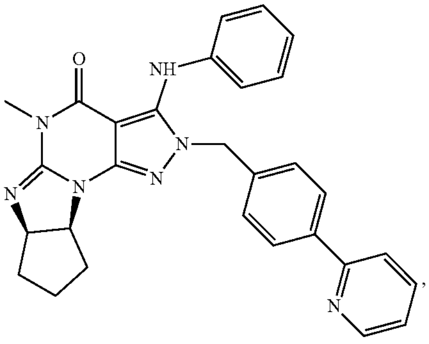

,

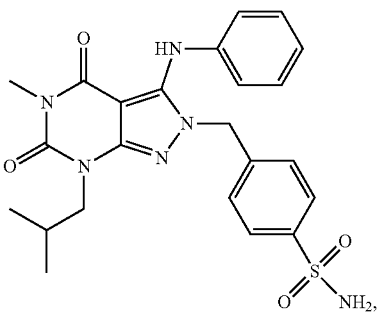

-continued
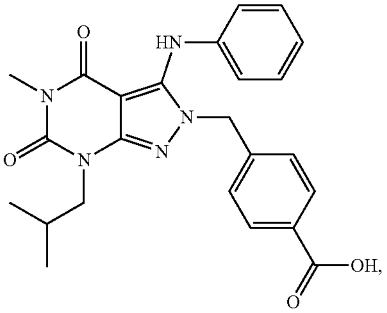
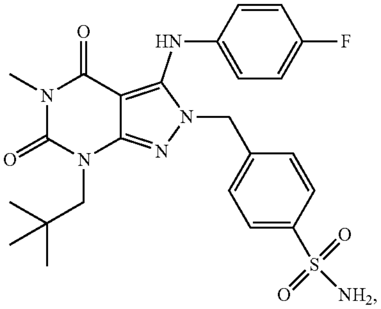
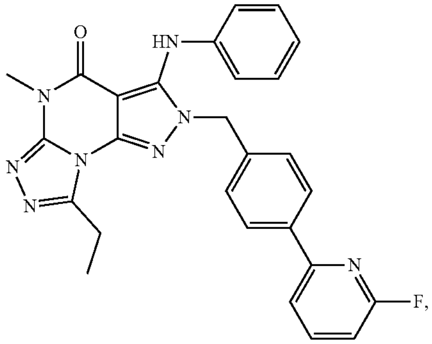
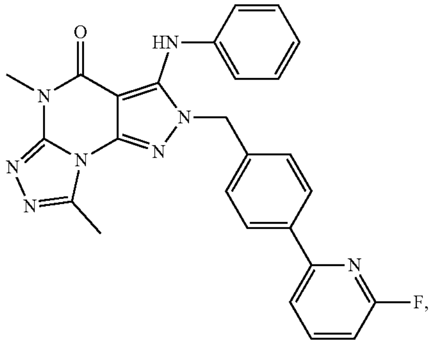
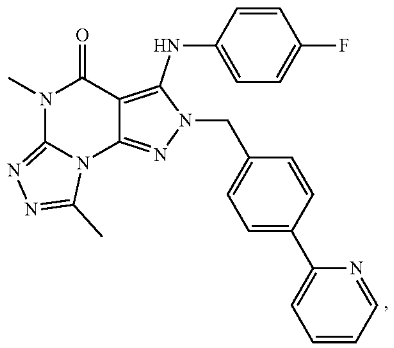
-continued
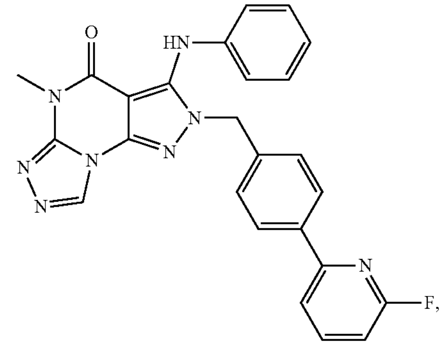
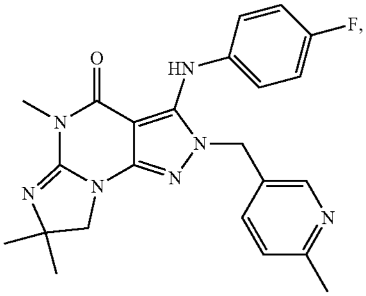
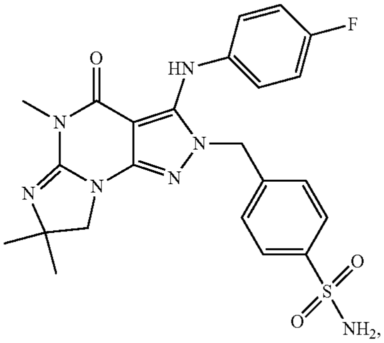
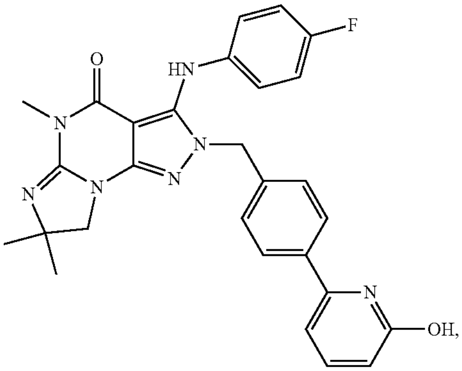

-continued
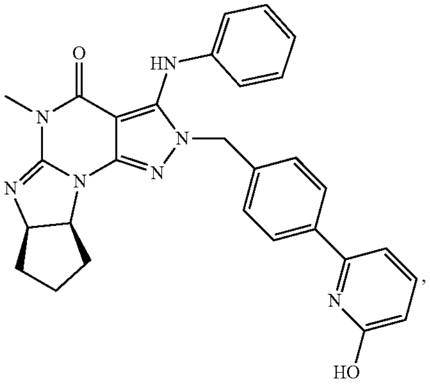
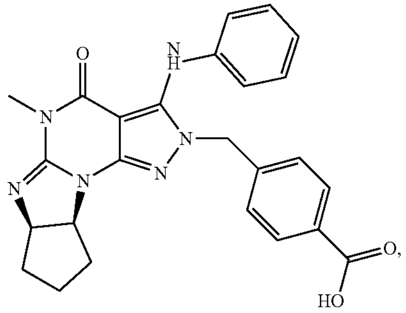
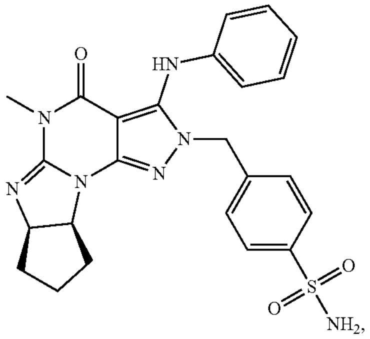
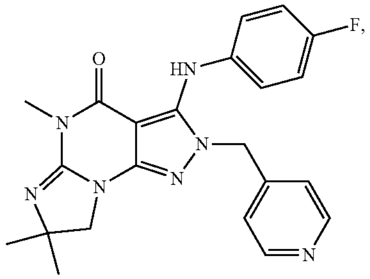
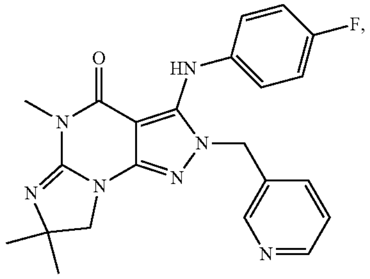
-continued
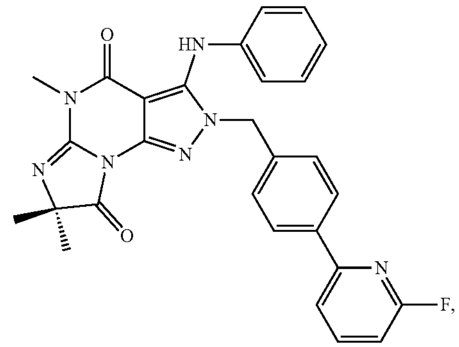
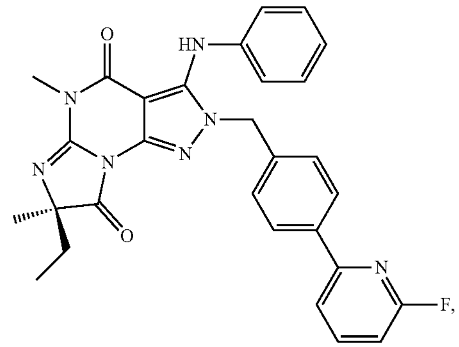
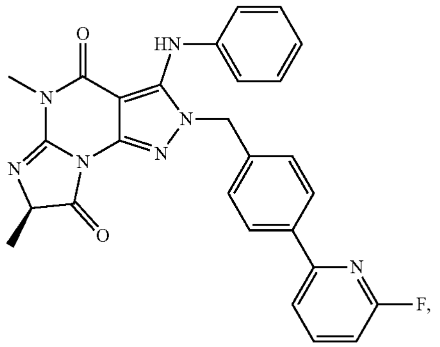
or
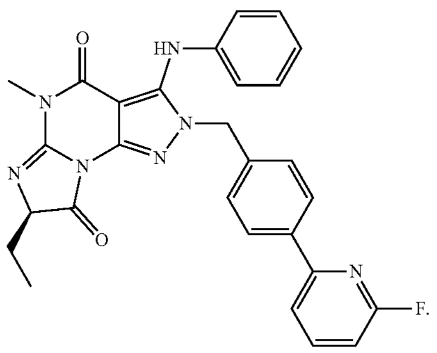
In one embodiment the invention provides administration of a PDE1 inhibitor for treatment or prophylaxis of inflammation or an inflammatory related disease or disorder, wherein the inhibitor is a compound according to the following:

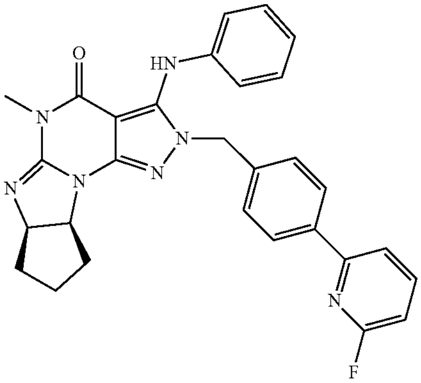 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

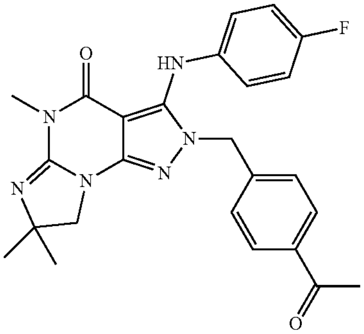 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

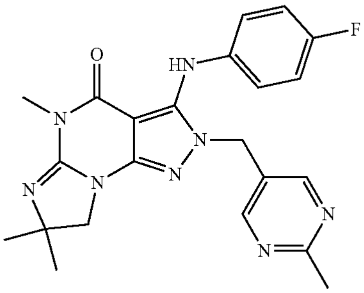 [SMILES: Cc1ncc(Cn2nc3c(c2Nc2ccc(F)cc2)C(=O)N(C)C2=NC(C)(C)CN23)cn1]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

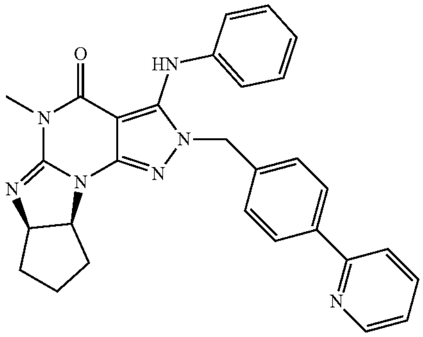 [SMILES: CN1C(=O)c2c(nn(Cc3ccc(-c4ccccn4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for treatment or prophylaxis of inflammation or an inflammatory related disease or disorder, wherein the inhibitor is a compound according to the following:

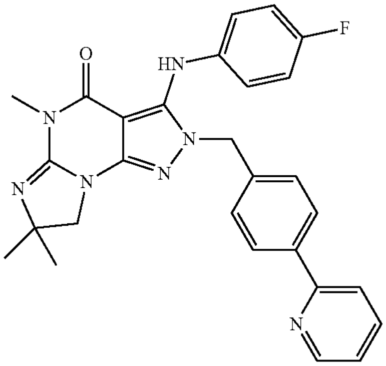 [SMILES: CN1C(=O)c2c(nn(Cc3ccc(-c4ccccn4)cc3)c2Nc2ccc(F)cc2)N2CC(C)(C)N=C12]

in free or pharmaceutically acceptable salt form.

In one embodiment, selective PDE1 inhibitors of any of the preceding formulae (e.g., Formula I, Ia, II, III, IV, V, VI and/or VII) are compounds that inhibit phosphodiesterase-mediated (e.g., PDE1-mediated, especially PDE1B-mediated) hydrolysis of cGMP, e.g., the preferred compounds have an $IC_{50}$ of less than 1 μM, preferably less than 500 nM, preferably less than 50 nM, and preferably less than 5 nM in an immobilized-metal affinity particle reagent PDE assay, in free or salt form.

In other embodiments, the invention provides administration of a PDE1 inhibitor for treatment of a condition selected from a cancer or tumor; for inhibiting the proliferation, migration and/or invasion of tumorous cells; and/or for treating a glioma, wherein the inhibitor is a compound according to the following:

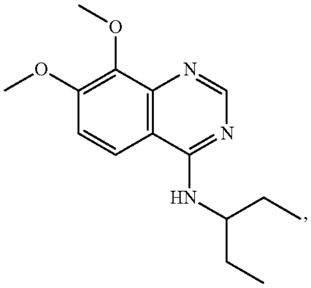

-continued

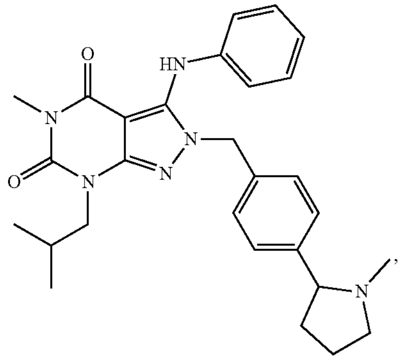

,

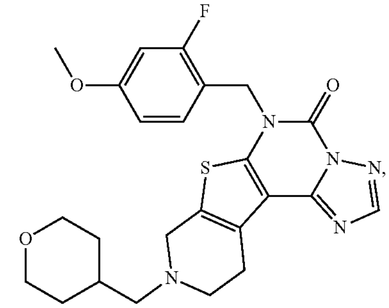

,

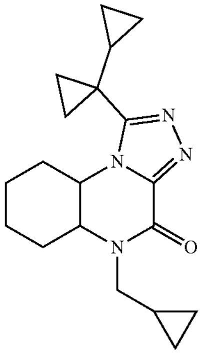

or

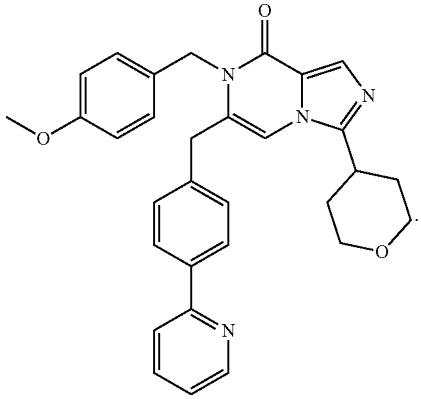

.

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; U.S. Publication 2017/0291901A1; International Publication WO2018/115067; U.S. Publication 2018/0179200A; U.S. Publication US20160318910A1; U.S. Pat. No. 9,868,741; International Publication WO2017/139186A1; International Application WO2016/040083; U.S. Publication 2017/0240532; International Publication WO 2016033776A1; U.S. Publication 2017/0233373; International Publication WO2015130568; International Publication WO2014159012; U.S. Pat. Nos. 9,034,864; 9,266,859; International Publication WO2009085917; U.S. Pat. No. 8,084,261; International Publication WO2018039052; U.S. Publication US20180062729; and International Publication WO2019027783 each of which are incorporated by reference in their entirety. In any situation in which the statements of any documents incorporated by reference contradict or are incompatible with any statements made in the present disclosure, the statements of the present disclosure shall be understood as controlling.

Still further examples of PDE1 inhibitors and suitable methods of use are disclosed in International Application PCT/US2019/033941 and U.S. Provisional Application 62/789,499, both of which are incorporated by reference herein.

If not otherwise specified or clear from context, the following terms herein have the following meanings:

(a) "Selective PDE1 inhibitor" as used herein refers to a PDE1 inhibitor with at least 100-fold selectivity for PDE1 inhibition over inhibition of any other PDE isoform.

(b) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(c) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(d) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(e) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(f) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

Compounds of the Disclosure, e.g., PDE1 inhibitors as described herein, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included.

Compounds of the Disclosure may in some cases also exist in prodrug form. A prodrug form is compound which converts in the body to a Compound of the Disclosure. For example, when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Disclosure contains a carboxylic acid, for example, Compound-C(O)OH, the acid ester prodrug of such compound, Compound-C(O)O—C1-4alkyl can hydrolyze to form Compound-C(O)OH and HO—C1-4alkyl. As will be appreciated the term thus embraces conventional pharmaceutical prodrug forms.

In another embodiment, the disclosure further provides a pharmaceutical composition comprising a PDE1 inhibitor in combination with an antitumor agent, each in free or pharmaceutically acceptable salt form, in admixture with a pharmaceutically acceptable carrier. The term "combination," as used herein, embraces simultaneous, sequential, or contemporaneous administration of the PDE1 inhibitor and the antitumor agent. In another embodiment, the disclosure provides a pharmaceutical composition containing such a compound. In some embodiments, the combination of the PDE1 inhibitor and the antitumor agent allows the antitumor agent to be administered in a dosage lower than would be effective if administered as sole monotherapy.

Methods of Using Compounds of the Disclosure

In another embodiment, the present application provides for a method (Method 1) of treating colon cancer comprising administering a pharmaceutically acceptable amount of a PDE1 inhibitor (i.e., PDE1 inhibitor according to Formula I, Ia, II, III, IV, V, VI and/or VII) to a subject in need thereof.

1.1 Method 1, wherein the colon cancer is colorectal cancer.

1.2 Any preceding method, further comprising the step of administering an antitumor agent to the patient.

1.3 Method 1.2, wherein the antitumor agent is administered concurrently with the PDE1 inhibitor.

1.4 Method 1.2, wherein the antitumor agent is administered prior to administering the PDE1 inhibitor.

1.5 Method 1.2, wherein the antitumor agent is administered after administering the PDE1 inhibitor.

1.6 Any of the preceding methods, wherein the PDE1 inhibitor, and optionally the antitumor agent, is administered with radiation therapy or chemotherapy.

1.7 Any of the preceding methods, wherein the PDE1 inhibitor, and optionally the antitumor agent, is administered concurrently with radiation therapy or chemotherapy.

1.8 Any of the preceding methods, wherein the PDE1 inhibitor, and optionally the antitumor agent, is administered prior to radiation therapy or chemotherapy.

1.9 Any of the preceding methods, wherein the PDE1 inhibitor, and optionally the antitumor agent, is administered after radiation therapy or chemotherapy.

1.10 Any of the preceding methods, wherein the PDE1 inhibitor is administered together with an antitumor agent, chemotherapeutic, gene therapeutic and/or immunologic treatment.

1.11 Any of the preceding methods, wherein administration of the PDE1 inhibitor is effective to induce one or more of the following in the colon cancer: apoptotic cell death, inhibition of migration, inhibition of metastasis, and/or reduction of inflammation.

1.12 Any of the preceding methods, wherein the PDE1 inhibitor is administered together with an antitumor agent, chemotherapeutic, gene therapeutic, immunologic treatment, corticosteroid, and/or an antihistamine.

1.13 Any of the preceding methods, wherein the colon cancer is mediated by PDE.

1.14 Any of the preceding methods, wherein the colon cancer is mediated by PDE1.

1.15 Any of the preceding methods, wherein the colon cancer is mediated by PDE1C.

1.16 Any of the preceding methods, wherein the colon cancer is characterized by a loss of calcium/calmodulin control.

1.17 Any of the preceding methods, wherein the subject is a human.

The disclosure further provides a PDE1 inhibitor for use in a method for treating a colon cancer, e.g., for use in any of Methods 1, et seq.

The disclosure further provides the use of a PDE1 inhibitor in the manufacture of a medicament for use in a method of treating a colon cancer, e.g., a medicament for use in any of Methods 1, et seq.

The invention further provides a pharmaceutical composition comprising a PDE1 inhibitor, e.g., any of a Compound of Formula I, Ia, II, III, IV, V, VI and/or VII, for use in any of Methods 1, et seq.

In another embodiment, the present application provides for a method (Method 2) of inhibiting the proliferation, migration and/or invasion of cancerous or tumorous cells in the colon comprising administering a pharmaceutically acceptable amount of a PDE1 inhibitor (i.e., PDE1 inhibitor according to Formula I, Ia, II, III, IV, V, VI and/or VII) to a subject in need thereof.

2.1 Method 2, wherein the method is for inhibiting the proliferation of cancerous or tumorous cells.
2.2 Any preceding method, wherein the subject is suffering from colon cancer.
2.3 Any preceding method, wherein the subject is suffering from colorectal cancer.
2.4 Any preceding method, further comprising the step of administering an antitumor agent to the patient.
2.5 Method 2.4, wherein the antitumor agent is administered concurrently with the PDE1 inhibitor.
2.6 Method 2.4, wherein the antitumor agent is administered prior to administering the PDE1 inhibitor.
2.7 Method 2.4, wherein the antitumor agent is administered after administering the PDE1 inhibitor.
2.8 Any of the preceding methods, wherein the PDE1 inhibitor, and optionally the antitumor agent, is administered with radiation therapy or chemotherapy.
2.9 Any of the preceding methods, wherein the PDE1 inhibitor, and optionally the antitumor agent, is administered concurrently with radiation therapy or chemotherapy.
2.10 Any of the preceding methods, wherein the PDE1 inhibitor, and optionally the antitumor agent, is administered prior to radiation therapy or chemotherapy.
2.11 Any of the preceding methods, wherein the PDE1 inhibitor, and optionally the antitumor agent, is administered after radiation therapy or chemotherapy.
2.12 Any of the preceding methods, wherein the PDE1 inhibitor is administered together with an antitumor agent, chemotherapeutic, gene therapeutic and/or immunologic treatment.
2.13 Any of the preceding methods, wherein the PDE1 inhibitor is administered together with an antitumor agent, chemotherapeutic, gene therapeutic, immunologic treatment, corticosteroid, and/or an antihistamine.
2.14 Any of the preceding methods, wherein the cancerous or tumorous cells in the colon are mediated by PDE.
2.15 Any of the preceding methods, wherein the cancerous or tumorous cells in the colon are mediated by PDE1.
2.16 Any of the preceding methods, wherein the cancerous or tumorous cells in the colon are mediated by PDE1C.
2.17 Any of the preceding methods, further including the step of assessing a subject's degree of calcium/calmodulin sensitivity in expressed PDE1, restoration of cyclic nucleotide levels, RNA expression of PDE1 or mutation of a PDE1 gene.
2.18 Any of the preceding methods, wherein the subject is a human.

The disclosure further provides a PDE1 inhibitor for use in a method for inhibiting the proliferation, migration and/or invasion of cancerous or tumorous cells, e.g., for use in any of Methods 2, et seq.

The disclosure further provides the use of a PDE1 inhibitor in the manufacture of a medicament for use in a method of inhibiting the proliferation, migration and/or invasion of cancerous or tumorous cells, e.g., a medicament for use in any of Methods 2, et seq.

The invention further provides a pharmaceutical composition comprising a PDE1 inhibitor, e.g., any of a Compound of Formula I, Ia, II, III, IV, V, VI and/or VII, for use in any of Methods 2, et seq.

In another embodiment, the present application provides for a method (Method 3) of treating a condition selected from a cancer or tumor cancer comprising administering a pharmaceutically acceptable amount of a PDE1 inhibitor (i.e., PDE1 inhibitor according to Formula I, Ia, II, III, IV, V, VI and/or VII) and a checkpoint inhibitor to a subject in need thereof.

3.1 Method 3, wherein the cancer is a colon cancer.
3.2 Any preceding method, wherein the cancer is colorectal cancer.
3.3 Any of the preceding methods, wherein the PDE1 inhibitor and the checkpoint inhibitor are administered with radiation therapy or chemotherapy.
3.4 Any of the preceding methods, wherein the PDE1 inhibitor and the checkpoint inhibitor are administered concurrently with radiation therapy or chemotherapy.
3.5 Any of the preceding methods, wherein the PDE1 inhibitor and the checkpoint inhibitor are administered prior to radiation therapy or chemotherapy.
3.6 Any of the preceding methods, wherein the PDE1 inhibitor, and the checkpoint inhibitor are administered after radiation therapy or chemotherapy.
3.7 Any of the preceding methods, wherein the PDE1 inhibitor and checkpoint inhibitor are administered together with an additional antitumor agent, chemotherapeutic, gene therapeutic and/or immunologic treatment.
3.8 Any of the preceding methods, wherein administration of the PDE1 inhibitor is effective to induce one or more of the following in the colon cancer: apoptotic cell death, inhibition of migration, inhibition of metastasis, and/or reduction of inflammation.
3.9 Any of the preceding methods, wherein the PDE1 inhibitor is administered together with an antitumor agent, chemotherapeutic, gene therapeutic, immunologic treatment, corticosteroid, and/or an antihistamine.
3.10 Any of the preceding methods, wherein the colon cancer is mediated by PDE.
3.11 Any of the preceding methods, wherein the colon cancer is mediated by PDE1.
3.12 Any of the preceding methods, wherein the colon cancer is mediated by PDE1C.
3.13 Any of the preceding methods, wherein the checkpoint inhibitor is an inhibitor of CTLA-4, PD-1 and/or PD-L1.
3.14 Any of the preceding methods, wherein the checkpoint inhibitor is selected from nivolumab, pembrolizumab, cemiplimab, ipilimumab, avelumab, durvalumab, atezolizumab, spartalizumab, or combinations thereof.
3.15 Any of the preceding methods, wherein the colon cancer is characterized by a loss of calcium/calmodulin control.
3.16 Any of the preceding methods, wherein the subject is a human.
3.17 Any of the preceding methods, wherein the PDE1 inhibitor is administered in an amount sufficient to reduce infiltration of monocytes and/or macrophages to a tumor associated microenvironment.
3.18 Any of the preceding methods, wherein the PDE1 inhibitor and the checkpoint inhibitor are administered in amounts together sufficient to reduce infiltration of monocytes and/or macrophages to a tumor associated microenvironment and/or to increase the infiltration of natural killer cells and $CD4^+$ T cells (i.e., TNFα-producing $CD4^+$ T cells).

3.19 Any of the preceding methods, wherein the PDE1 inhibitor is administered in an amount of about 1-1000 mg/kg, e.g., about 250-750 mg/kg, e.g., about 400-600 mg/kg, e.g., about 500 mg/kg.

The disclosure further provides a PDE1 inhibitor for use in a method for inhibiting the proliferation, migration and/or invasion of cancerous or tumorous cells, e.g., for use in any of Methods 3, et seq.

The disclosure further provides the use of a PDE1 inhibitor in the manufacture of a medicament for use in a method of inhibiting the proliferation, migration and/or invasion of cancerous or tumorous cells, e.g., a medicament for use in any of Methods 3, et seq.

The invention further provides a pharmaceutical composition comprising a PDE1 inhibitor, e.g., any of a Compound of Formula I, Ia, II, III, IV, V, VI and/or VII, for use in any of Methods 3, et seq.

In some embodiments, the pharmaceutical compositions are administered in combination with one or more antitumor drugs, for example, drugs known to have an effect in treating or eliminating various types of cancers and/or tumors. Non-limiting examples of antitumor drugs are Abemaciclib, Abiraterone Acetate, Abitrexate™ (Methotrexate), Abraxane® (Paclitaxel Albumin-stabilized Nanoparticle Formulation), ABVD, ABVE, ABVE-PC, AC, Acalabrutinib, AC-T, Adcetris® (Brentuximab Vedotin), ADE, Ado-Trastuzumab Emtansine, Adriamycin® (Doxorubicin Hydrochloride), Afatinib Dimaleate, Afinitor® (Everolimus), Akynzeo® (Netupitant and Palonosetron Hydrochloride), Aldara® (Imiquimod), Aldesleukin, Alecensa® (Alectinib), Alectinib, Alemtuzumab, Alimta® (Pemetrexed Disodium), Aliqopa® (Copanlisib Hydrochloride), Alkeran® for Injection (Melphalan Hydrochloride), Alkeran® Tablets (Melphalan), Aloxi® (Palonosetron Hydrochloride), Alunbrig® (Brigatinib), Ambochlorin (Chlorambucil), Amifostine, Aminolevulinic Acid, Anastrozole, Aprepitant, Aredia [,]® (Pamidronate Disodium), Arimidex® (Anastrozole), Aromasin® (Exemestane), Arranon® (Nelarabine), Arsenic Trioxide, Arzerra® (Ofatumumab), Asparaginase *Erwinia chrysanthemi*, Atezolizumab, Avastin® (Bevacizumab), Avelumab, Axicabtagene Ciloleucel, Axitinib, Azacitidine, Bavencio® (Avelumab), BEACOPP, Beleodaq® (Belinostat), Belinostat, Bendamustine Hydrochloride, BEP, Besponsa® (Inotuzumab Ozogamicin), Bevacizumab, Bexarotene, Bicalutamide, BiCNU® (Carmustine), Bleomycin, Blinatumomab, Blincyto® (Blinatumomab), Bortezomib, Bosulif® (Bosutinib), Bosutinib, Brentuximab Vedotin, Brigatinib, BuMel, Busulfan, Busulfex® (Busulfan), Cabazitaxel, Cabometyx® (Cabozantinib-S-Malate), Cabozantinib-S-Malate, CAF, Calquence® (Acalabrutinib), Campath® (Alemtuzumab), Camptosar® (Irinotecan Hydrochloride), Capecitabine, CAPOX, Carac® (Fluorouracil—Topical), Carboplatin, CARBOPLATIN-TAXOL, Carfilzomib, Carmubris (Carmustine), Carmustine, Carmustine Implant, Casodex® (Bicalutamide), CEM, Ceritinib, Cerubidine® (Daunorubicin Hydrochloride), Cervarix® (Recombinant HPV Bivalent Vaccine), Cetuximab, CEV, Chlorambucil, CHLORAMBUCIL-PREDNISONE, CHOP, Cisplatin, Cladribine, Clafen® (Cyclophosphamide), Clofarabine, Clofarex™ (Clofarabine), Clolar® (Clofarabine), CMF, Cobimetinib, Cometriq® (Cabozantinib-S-Malate), Copanlisib Hydrochloride, COPDAC, COPP, COPP-ABV, Cosmegen® (Dactinomycin), Cotellic® (Cobimetinib), Crizotinib, CVP, Cyclophosphamide, Cyfos™ (Ifosfamide), Cyramza® (Ramucirumab), Cytarabine, Cytarabine Liposome, Cytosar-U™ (Cytarabine), Cytoxan™ (Cyclophosphamide), Dabrafenib, Dacarbazine, Dacogen® (Decitabine), Dactinomycin, Daratumumab, Darzalex® (Daratumumab), Dasatinib, Daunorubicin Hydrochloride, Daunorubicin Hydrochloride and Cytarabine Liposome, Decitabine, Defibrotide Sodium, Defitelio® (Defibrotide Sodium), Degarelix, Denileukin Diftitox, Denosumab, DepoCyt™ (Cytarabine Liposome), Dexamethasone, Dexrazoxane Hydrochloride, Dinutuximab, Docetaxel, Doxil® (Doxorubicin Hydrochloride Liposome), Doxorubicin Hydrochloride, Doxorubicin Hydrochloride Liposome, Dox-SLIM (Doxorubicin Hydrochloride Liposome), DTIC-Dome™ (Dacarbazine), Durvalumab, Efudex® (Fluorouracil—Topical), Elitek® (Rasburicase), Ellence® (Epirubicin Hydrochloride), Elotuzumab, Eloxatin® (Oxaliplatin), Eltrombopag Olamine, Emend® (Aprepitant), Empliciti® (Elotuzumab), Enasidenib Mesylate, Enzalutamide, Epirubicin Hydrochloride, EPOCH, Erbitux® (Cetuximab), Eribulin Mesylate, Erivedge® (Vismodegib), Erlotinib Hydrochloride, Erwinaze® (Asparaginase *Erwinia chrysanthemi*), Ethyol® (Amifostine), Etopophos® (Etoposide Phosphate), Etoposide, Etoposide Phosphate, Evacet™ (Doxorubicin Hydrochloride Liposome), Everolimus, Evista® (Raloxifene Hydrochloride), Evomela® (Melphalan Hydrochloride), Exemestane, 5-FU (Fluorouracil Injection), 5-FU (Fluorouracil—Topical), Fareston® (Toremifene), Farydak® (Panobinostat), Faslodex® (Fulvestrant), FEC, Femara® (Letrozole), Filgrastim, Fludara™ (Fludarabine Phosphate), Fludarabine Phosphate, Fluoroplex® (Fluorouracil—Topical), Fluorouracil Injection, Fluorouracil—Topical, Flutamide, Folex™ (Methotrexate), Folex PFS™ (Methotrexate), Folfiri, Folfiri-Bevacizumab, Folfiri-Cetuximab, Folfirinox, Folfox, Folotyn® (Pralatrexate), FU-LV, Fulvestrant, Gardasil® (Recombinant HPV Quadrivalent Vaccine), Gardasil® 9 (Recombinant HPV Nonavalent Vaccine), Gazyva® (Obinutuzumab), Gefitinib, Gemcitabine Hydrochloride, Gemcitabine-Cisplatin, Gemcitabine-Oxaliplatin, Gemtuzumab Ozogamicin, Gemzar™ (Gemcitabine Hydrochloride), Gilotrif® (Afatinib Dimaleate), Gleevec® (Imatinib Mesylate), Gliadel® (Carmustine Implant), Gliadel® wafer (Carmustine Implant), Glucarpidase, Goserelin Acetate, Halaven® (Eribulin Mesylate), Hemangeol® (Propranolol Hydrochloride), Herceptin® (Trastuzumab), HPV Bivalent Vaccine, Recombinant, HPV Nonavalent Vaccine, Recombinant, HPV Quadrivalent Vaccine, Recombinant, Hycamtin® (Topotecan Hydrochloride), Hydrea® (Hydroxyurea), Hydroxyurea, Hyper-CVAD, Ibrance® (Palbociclib), Ibritumomab Tiuxetan, Ibrutinib, ICE, Iclusig® (Ponatinib Hydrochloride), Idamycin™ (Idarubicin Hydrochloride), Idarubicin Hydrochloride, Idelalisib, Idhifa® (Enasidenib Mesylate), Ifex® (Ifosfamide), Ifosfamide, Ifosfamidum (Ifosfamide), IL-2 (Aldesleukin), Imatinib Mesylate, Imbruvica® (Ibrutinib), Imfinzi® (Durvalumab), Imiquimod, Imlygic® (Talimogene Laherparepvec), Inlyta® (Axitinib), Inotuzumab Ozogamicin, Interferon Alfa-2b, Recombinant, Interleukin-2 (Aldesleukin), Intron® A (Recombinant Interferon Alfa-2b), Ipilimumab, Iressa® (Gefitinib), Irinotecan Hydrochloride, Irinotecan Hydrochloride Liposome, Istodax® (Romidepsin), Ixabepilone, Ixazomib Citrate, Ixempra™ (Ixabepilone), Jakafi® (Ruxolitinib Phosphate), JEB, Jevtana® (Cabazitaxel), Kadcyla® (Ado-Trastuzumab Emtansine), Keoxifene (Raloxifene Hydrochloride), Kepivance® (Palifermin), Keytruda® (Pembrolizumab), Kisqali® (Ribociclib), Kymriah® (Tisagenlecleucel), Kyprolis® (Carfilzomib), Lanreotide Acetate, Lapatinib Ditosylate, Lartruvo (Olaratumab), Lenalidomide, Lenvatinib Mesylate, Lenvima® (Lenvatinib Mesylate), Letrozole, Leucovorin Calcium, Leukeran® (Chlorambucil), Leuprolide Acetate, Leustatin® (Cladribine), Levulan® (Aminolevulinic Acid), Linfolizin (Chlorambucil), LipoDox® (Doxorubicin Hydrochloride Liposome), Lomustine, Lonsurf® (Trifluridine and Tipiracil Hydrochloride), Lupron™ (Leuprolide Acetate), Lupron Depot® (Leuprolide Acetate), Lupron Depot-Ped® (Leuprolide Acetate), Lynparza® (Olaparib), Marqibo® (Vincristine Sulfate Liposome), Matulane® (Procarbazine Hydrochloride), Mechlorethamine Hydrochloride, Megestrol Acetate, Mekinist® (Trametinib), Melphalan, Melphalan Hydrochloride, Mercaptopurine, Mesna, Mesnex® (Mesna), Methazolastone (Temozolomide), Methotrexate, Methotrexate LPF (Methotrexate), Methylnaltrexone Bromide, Mexate™ (Methotrexate), Mexate™-AQ (Methotrexate), Midostaurin, Mitomycin C, Mitoxantrone Hydrochloride, Mitozytrex™ (Mitomycin C), MOPP, Mozobil® (Plerixafor), Mustargen™ (Mechlorethamine Hydrochloride), Mutamycin™ (Mitomycin C), Myleran® (Busulfan), Mylosar™ (Azacitidine), Mylotarg® (Gemtuzumab Ozogamicin), Nanoparticle Paclitaxel (Paclitaxel Albumin-stabilized Nanoparticle Formulation), Navelbine® (Vinorelbine Tartrate), Necitumumab, Nelarabine, Neosar™ (Cyclophosphamide), Neratinib Maleate, Nerlynx® (Neratinib Maleate), Netupitant and Palonosetron Hydrochloride, Neulasta® (Pegfilgrastim), Neupogen® (Filgrastim), Nexavar® (Sorafenib Tosylate), Nilandron® (Nilutamide), Nilotinib, Nilutamide, Ninlaro® (Ixazomib Citrate), Niraparib Tosylate Monohydrate, Nivolumab, Nolvadex™ (Tamoxifen Citrate), Nplate® (Romiplostim), Obinutuzumab, Odomzo® (Sonidegib), OEPA, Ofatumumab, OFF, Olaparib, Olaratumab (Lartruvo), Omacetaxine Mepesuccinate, Oncaspar® (Pegaspargase), Ondansetron Hydrochloride, Onivyde® (Irinotecan Hydrochloride Liposome), Ontak™ (Denileukin Diftitox), Opdivo™ (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin® (Carboplatin), Pazopanib Hydrochloride, PCV, PEB, Pegaspargase, Pegfilgrastim, Peginterferon Alfa-2b, PEG-Intron™ (Peginterferon Alfa-2b), Pembrolizumab, Pemetrexed Disodium, Perjeta® (Pertuzumab), Pertuzumab, Platinol™ (Cisplatin), Platinol™-AQ (Cisplatin), Plerixafor, Pomalidomide, Pomalyst® (Pomalidomide), Ponatinib Hydrochloride, Portrazza® (Necitumumab), Pralatrexate, Prednisone, Procarbazine Hydrochloride, Proleukin® (Aldesleukin), Prolia® (Denosumab), Promacta® (Eltrombopag Olamine), Propranolol Hydrochloride, Provenge® (Sipuleucel-T), Purinethol® (Mercaptopurine), Purixan® (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor® (Methylnaltrexone Bromide), R-EPOCH, Revlimid® (Lenalidomide), Rheumatrex™ (Methotrexate), Ribociclib, R-ICE, Rituxan® (Rituximab), Rituxan Hycela® (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca® (Rucaparib Camsylate), Rucaparib Camsylate, Ruxolitinib Phosphate, Rydapt® (Midostaurin), Sclerosol™ Intrapleural Aerosol (Talc), Siltuximab, Sipuleucel-T, Somatuline Depot® (Lanreotide Acetate), Sonidegib, Sorafenib Tosylate, Sprycel® (Dasatinib), STANFORD® V, Sterile Talc Powder (Talc), Steritalc® (Talc), Stivarga® (Regorafenib), Sunitinib Malate, Sutent® (Sunitinib Malate), Sylatron™ (Peginterferon Alfa-2b), Sylvant® (Siltuximab), Synribo™ (Omacetaxine Mepesuccinate), Tabloid® (Thioguanine), TAC, Tafinlar® (Dabrafenib), Tagrisso® (Osimertinib), Talc, Talimogene Laherparepvec, Tamoxifen Citrate, Tarabine PFS™ (Cytarabine), Tarceva® (Erlotinib Hydrochloride), Targretin® (Bexarotene), Tasigna® (Nilotinib), Taxol® (Paclitaxel), Taxotere® (Docetaxel), Tecentriq® (Atezolizumab), Temodar® (Temozolomide), Temozolomide, Temsirolimus, Thalidomide, Thalomid® (Thalidomide), Thioguanine, Thiotepa, Tisagenlecleucel, Tolak® (Fluorouracil—Topical), Topotecan Hydrochloride, Toremifene, Torisel® (Temsirolimus), Totect® (Dexrazoxane Hydrochloride), TPF, Trabectedin, Trametinib, Trastuzumab, Treanda® (Bendamustine Hydrochloride), Trifluridine and Tipiracil Hydrochloride, Trisenox® (Arsenic Trioxide), Tykerb® (Lapatinib Ditosylate), Unituxin® (Dinutuximab), Uridine Triacetate, VAC, Valrubicin, Valstar® (Valrubicin), Vandetanib, VAMP, Varubi® (Rolapitant Hydrochloride), Vectibix® (Panitumumab), VeIP, Velban™ (Vinblastine Sulfate), Velcade® (Bortezomib), Velsar™ (Vinblastine Sulfate), Vemurafenib, Venclexta® (Venetoclax), Venetoclax, Verzenio® (Abemaciclib), Viadur™ (Leuprolide Acetate), Vidaza® (Azacitidine), Vinblastine Sulfate, Vincasar PFS® (Vincristine Sulfate), Vincristine Sulfate, Vincristine Sulfate Liposome, Vinorelbine Tartrate, VIP, Vismodegib, Vistogard® (Uridine Triacetate), Voraxaze® (Glucarpidase), Vorinostat, Votrient® (Pazopanib Hydrochloride), Vyxeos® (Daunorubicin Hydrochloride and Cytarabine Liposome), Wellcovorin™ (Leucovorin Calcium), Xalkori® (Crizotinib), Xeloda® (Capecitabine), XELIRI, XELOX, Xgeva® (Denosumab), Xofigo® (Radium 223 Dichloride), Xtandi® (Enzalutamide), Yervoy® (Ipilimumab), Yescarta® (Axicabtagene Ciloleucel), Yondelis® (Trabectedin), Zaltrap® (Ziv-Aflibercept), Zarxio® (Filgrastim), Zejula® (Niraparib Tosylate Monohydrate), Zelboraf® (Vemurafenib), Zevalin® (Ibritumomab Tiuxetan), Zinecard® (Dexrazoxane Hydrochloride), Ziv-Aflibercept, Zofran® (Ondansetron Hydrochloride), Zoladex® (Goserelin Acetate), Zoledronic Acid, Zolinza® (Vorinostat), Zometa® (Zoledronic Acid), Zydelig® (Idelalisib), Zykadia® (Ceritinib), Zytiga® (Abiraterone Acetate).

As used herein, the term “antitumor agent” is understood to refer to any chemical agents or drugs effective in preventing or inhibiting the formation or growth of cancers or tumors. Antitumor agents as discussed herein may encompass alkylating agents, antimetabolites, natural products, hormones, and/or antibodies. Treatment of tumors or cancer may include limiting the proliferation, migration and/or invasion of cancerous or tumorous cells in the body, or limiting the symptoms associated with said cancer or tumor. As used herein, antitumor agents are understood to encompass and otherwise be synonymous with anticancer agents.

Methods of Making Compounds of the Disclosure

The PDE1 inhibitors of the Disclosure and their pharmaceutically acceptable salts may be made using the methods as described and exemplified in U.S. Pat. No. 8,273,750, US 2006/0173878, U.S. Pat. No. 8,273,751, US 2010/0273753, U.S. Pat. Nos. 8,697,710, 8,664,207, 8,633,180, 8,536,159, US 2012/0136013, US 2011/0281832, US 2013/0085123, US 2013/0324565, US 2013/0338124, US 2013/0331363, WO 2012/171016, and WO 2013/192556, and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various PDE1 inhibitors and starting materials therefor may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138. All references cited herein are hereby incorporated by reference in their entirety.

Further PDE1 inhibitors and related methods are disclosed in U.S. Provisional Application 62/833,481, which is hereby incorporated by reference in its entirety. Additional related PDE1 inhibitors and related methods are disclosed in International Publication WO2018/049417, which is hereby incorporated by reference in its entirety.

The Compounds of the Disclosure include their enantiomers, diastereomers and racemates, as well as their polymorphs, hydrates, solvates and complexes. Some individual compounds within the scope of this disclosure may contain double bonds. Representations of double bonds in this disclosure are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the disclosure is the $^{11}C$ isotope. These radio isotopes are useful for radio-imaging and/or pharmacokinetic studies of the compounds of the disclosure.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

The words "treatment" and "treating" are to be understood accordingly as embracing treatment or amelioration of symptoms of disease as well as treatment of the cause of the disease.

For methods of treatment, the word "effective amount" is intended to encompass a therapeutically effective amount to treat a specific disease or disorder.

The term "patient" include human or non-human (i.e., animal) patient. In particular embodiment, the disclosure encompasses both human and nonhuman. In another embodiment, the disclosure encompasses nonhuman. In other embodiment, the term encompasses human.

The term "comprising" as used in this disclosure is intended to be open-ended and does not exclude additional, un-recited elements or method steps.

Dosages employed in practicing the present disclosure will of course vary depending, e.g. on the particular disease or condition to be treated, the particular Compounds of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration of both the PDE1 inhibitor will accordingly be in the range of from about 0.50 to 300 mg, conveniently administered once, or in divided doses 2 to 4 times, daily or in sustained release form. Unit dosage forms for oral administration thus for example may comprise from about 0.2 to 150 or 300 mg, e.g. from about 0.2 or 2.0 to 10, 25, 50, 75 100, 150, or 200 mg of a Compound of the Disclosure, together with a pharmaceutically acceptable diluent or carrier therefor.

Compounds of the Disclosure, particularly for use or administration in any of Methods 1 or 2, et seq., may be administered at higher doses as necessary to treat a cancer or tumor, e.g., colorectal cancer. It is envisioned that administration of a PDE1 inhibitor for such a method may be in the range of about 50 mg to 1000 mg daily. For example, a patient being administered a PDE1 inhibitor for a condition according to any of Methods 1-6, et seq., may be administered a PDE1 inhibitor according to Formula I, Ia, II, III, IV, V, VI and/or VII in an amount of 50 mg to 1000 mg daily, 50 mg to 900 mg daily, 50 mg to 800 mg daily, 50 mg to 700 mg daily, 50 mg to 600 mg daily, 50 mg to 500 mg daily, 50 mg to 400 mg daily, 50 mg to 350 mg daily, 50 mg to 300 mg daily, 50 mg to 250 mg daily, 50 mg to 200 mg daily, 50 mg to 150 mg daily or 50 mg to 100 mg daily.

Compounds of the Disclosure may be administered by any satisfactory route, including orally, parenterally (intravenously, intramuscular or subcutaneous) or transdermally, but are preferably administered orally. In certain embodiments, the Compounds of the Disclosure, e.g., in depot formulation, is preferably administered parenterally, e.g., by injection.

The Compounds of the Disclosure and the Pharmaceutical Compositions of the Disclosure of the Disclosure may be used in combination with one or more additional therapeutic agents, particularly at lower dosages than when the individual agents are used as a monotherapy so as to enhance the therapeutic activities of the combined agents without causing the undesirable side effects commonly occur in conventional monotherapy. Therefore, the Compounds of the Disclosure may be simultaneously, separately, sequentially, or contemporaneously administered with other agents useful in treating disease. In another example, side effects may be reduced or minimized by administering a Compound of the Disclosure in combination with one or more additional therapeutic agents in free or salt form, wherein the dosages of (i) the second therapeutic agent(s) or (ii) both Compound of the Disclosure and the second therapeutic agent, are lower than if the agent/compound are administered as a monotherapy. By way of non-limiting example, such additional therapeutic agents may include ACE inhibitors, Angiotensin II receptor antagonists, calcium channel blockers, etc.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

Pharmaceutical compositions comprising Compounds of the Disclosure may be prepared using conventional diluents or excipients and techniques known in the galenic art. Thus, oral dosage forms may include tablets, capsules, solutions, suspensions and the like.

EXAMPLES

Example 1: Determining the Ability of PDE1 Inhibitors to Inhibit the Growth of Murine Colon Cancer Aliquots of cancerous cells are injected into the subscapular space of BALB/C mice to induce colon carcinoma. The tumors are allowed to grow for 7 days, when tumor volume is measured. Once a tumor has formed, drug treatment is initiated (50 mg/kg Compound 1, once daily, i.p. in 0.5% methylcellulose vehicle) and tumor growth is observed and recorded daily. Compounds 1 is shown below:

Compound 1

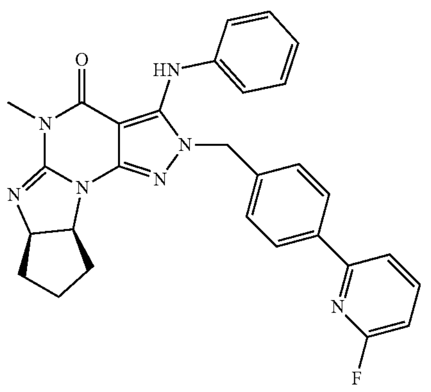

The mice were sacrificed at thirty days post-injection, and the tumors are isolated from the mice. As shown in FIG. 1, Compound 1 significantly slowed tumor growth in the CT26 cell samples after 30 days.

Figure 2:
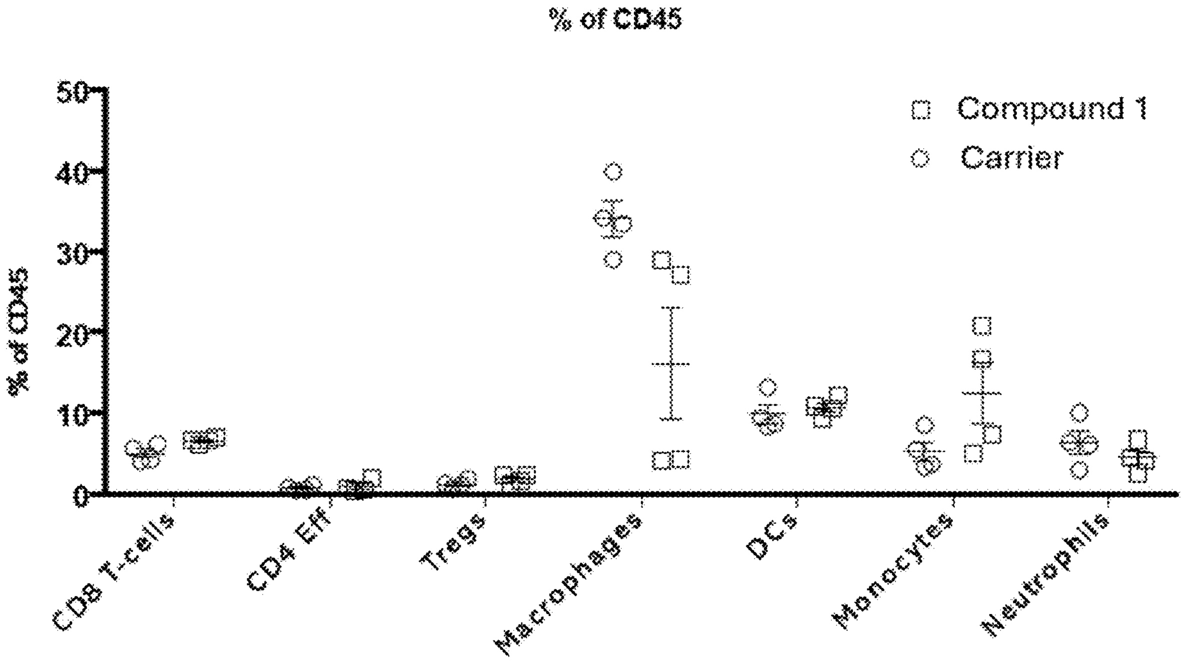
FIG. 2 shows the change in relative proportions of immune cells in CT26 murine cancer cells in samples treated with Compound 1 and untreated control.

The tumors were then enzymatically dissociated into a single cell suspensions, stained with fluorophore-tagged antibodies and are analyzed by flow cytometry. Cells were sorted and analyzed for immune markers. As shown in FIG. 2, treatment with Compound 1 led to significant increases in monocytes and CD8 T-cells, but a significant decrease was observed in macrophage presence in the tumor microenvironment. Without being bound by theory, it is believed that PDE1 inhibitors possess the ability to modulate immune function in the tumor microenvironment, one manner of which includes reducing tumor invasion by macrophages. In turn, it is believed this this allows the innate immune system to more efficiently target tumor cells, which is consistent with the results observed here (i.e., increased activation of T-cells in the tumor microenvironment).

Example 2: Analysis of Co-Administration of PDE1 Inhibitors with Checkpoint Inhibitors to Inhibit the Growth of Murine Cancer The effects of Compound 1, alone or combination with sub-effective doses of the checkpoint inhibitor, anti-PD-1, were assessed on the growth of CT26 xenograft tumors in BALB/c mice. Treatment-naïve tumor-bearing mice (i.e., isotype group) were compared with groups of mice receiving monotherapy of Compound 1 defined in Example 1, mice receiving a sub-effective dose of a checkpoint inhibitor (anti-PD-1 antibody), and mice receiving both Compound 1 and a sub-effective dose of anti-PD-1 antibody.

BALB/c mice were subcutaneously injected with CT26 cells at day 0 and then divided into four groups at day 7: (1) Compound 1 treatment, (50 mg/kg, i.p. qd), 5 days/week; (2) Isotype group, ip mlgG isotype at days 7, 10 and 14; (3) Anti-PD-1 group, administered i.p. at days 7, 10 and 14; and (4) Combination group, treated with Compound 1 and anti-PD-1 as group 1 and group 3. Tumor volumes were measured every 2 or 3 days. At day 17-18, tumors were excised, dissected, and used to make single cell suspensions. These tumor single cell suspensions were incubated with FC blocker (eBioscience) and then stained with antibodies on ice in the dark. Samples were acquired on a FACSCalibur, LSRII or LSRII yellow (BD Biosciences), and analyzed with FlowJo (Tree Star).

Zero out of nine mice in the isotype treated group showed tumor clearance (i.e., tumor showed a volume smaller than 100 $mm^3$), while one out of five mice in the Compound 1 treated group, and one out of ten mice in the anti-PD-1 treated group showed tumor clearance. However, seven out of fifteen mice in the Compound 1 and anti-PD-1 combination-treated group showed tumor clearance. At the end of experiments, tumors were also weighed. The results showed tumor weight in mice receiving combination therapy of Compound 1 and anti-PD-1 were significantly less than those in isotype treated control group.

Fluorescence-activated cell sorting (FACS) of tumor-infiltrating immune cells revealed that tumors from Compound 1 monotherapy-treated mice showed significantly decreased numbers of CD45+ tumor (infiltrating) macrophages and monocytes and that combination therapy of Compound 1 and anti-PD-1 enhanced anti-tumor immunity by eliciting increased numbers of CD45+ natural killer (NK) cells and TNFa-producing CD4 T-cells. The results suggest that Compound 1 alone is able to reduce tumor macrophages which enhances anti-tumor immunity of anti-PD-1.

Alternative combinations and variations of the examples provided will become apparent based on the disclosure. It is not possible to provide specific examples for all of the many possible variations of the embodiments described, but such combinations and variations may be claims that eventually issue.

What is claimed is:

1. A method of treating colon cancer or colorectal cancer comprising administering a pharmaceutically acceptable amount of a PDE1 inhibitor to a subject in need thereof, wherein the PDE1 inhibitor is a compound of Formula Ia Formula Ia

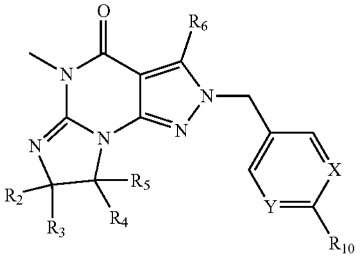

wherein (i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;

(ii) $R_6$ is (optionally halo-substituted) phenylamino, (optionally halo-substituted) benzylamino, $C_{1-4}$alkyl, or $C_{1-4}$alkyl sulfide;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and X and Y are independently C or N, in free, pharmaceutically acceptable salt or prodrug form, including its enantiomers, diastereoisomers and racemates.

2. A method of inhibiting the proliferation, migration and/or invasion of cancerous or tumorous cells in the colon comprising administering a pharmaceutically acceptable amount of a PDE1 inhibitor to a subject in need thereof, wherein the PDE1 inhibitor is a compound of formula Ia Formula Ia

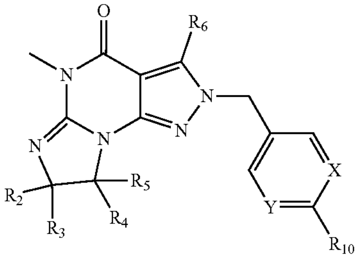

wherein (i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;

(ii) $R_6$ is (optionally halo-substituted) phenylamino, (optionally halo-substituted) benzylamino, $C_{1-4}$alkyl, or $C_{1-4}$alkyl sulfide;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and X and Y are independently C or N, in free, pharmaceutically acceptable salt or prodrug form, including its enantiomers, diastereoisomers and racemates.

3. The method according to claim 2, wherein the subject is suffering from colon cancer or colorectal cancer.

4. The method according to claim 1, wherein the PDE1 inhibitor is selected from any of the following:

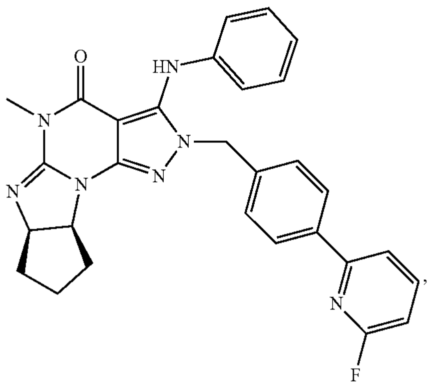

,

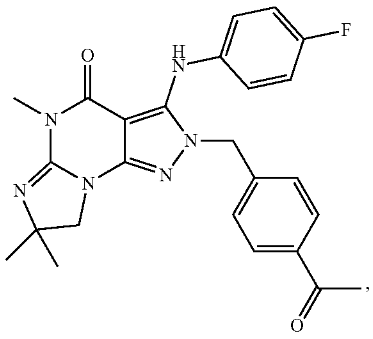

,

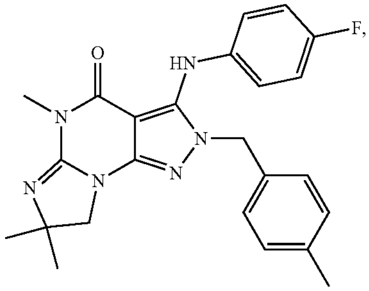

,

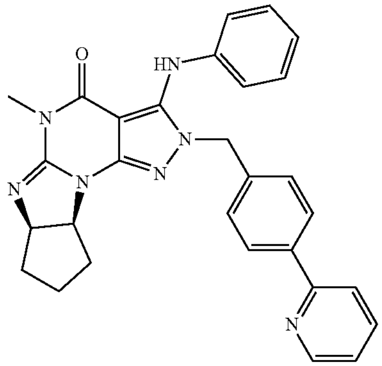

or

-continued

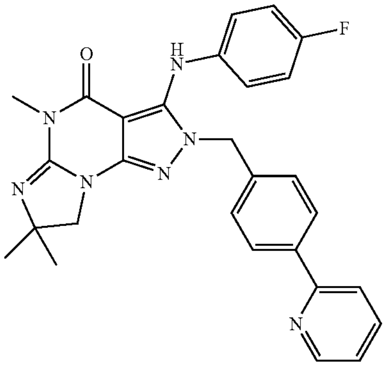

in free or pharmaceutically acceptable salt form.

5. The method according to claim 1, wherein the PDE1 inhibitor is administered in combination with an antitumor agent.

6. A method of treating colon cancer or colorectal cancer comprising administering a pharmaceutically acceptable amount of a PDE1 inhibitor and a checkpoint inhibitor to a subject in need thereof, wherein the PDE1 inhibitor is a compound of formula Ia Formula Ia

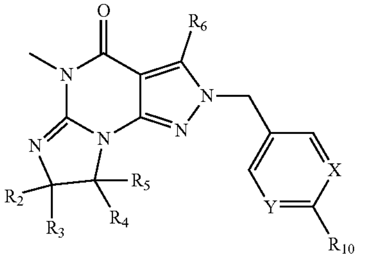

wherein (i) $R_2$ and $R_5$ are independently H or hydroxy and $R_3$ and $R_4$ together form a tri- or tetra-methylene bridge; or $R_2$ and $R_3$ are each methyl and $R_4$ and $R_5$ are each H; or $R_2$, $R_4$ and $R_5$ are H and $R_3$ is isopropyl;

(ii) $R_6$ is (optionally halo-substituted) phenylamino, (optionally halo-substituted) benzylamino, $C_{1-4}$alkyl, or $C_{1-4}$alkyl sulfide;

(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and X and Y are independently C or N, in free, pharmaceutically acceptable salt or prodrug form, including its enantiomers, diastereoisomers and racemates.

7. The method according to claim 6, wherein the PDE1 inhibitor is selected from any of the following:

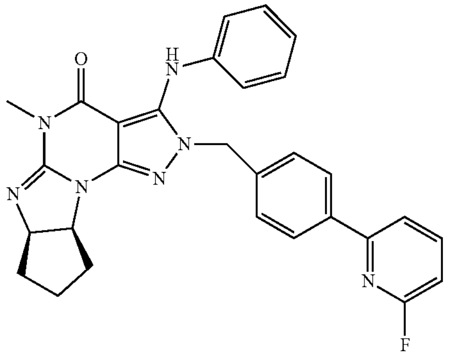

,

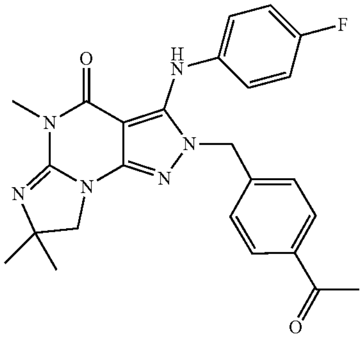

,

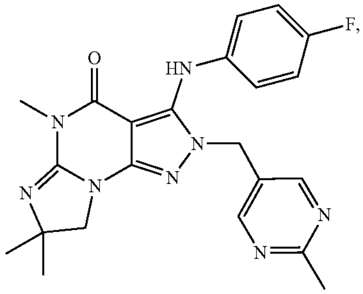

,

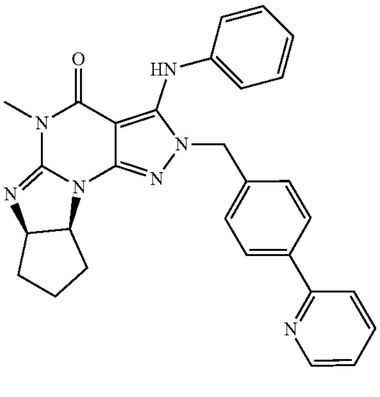

or

-continued

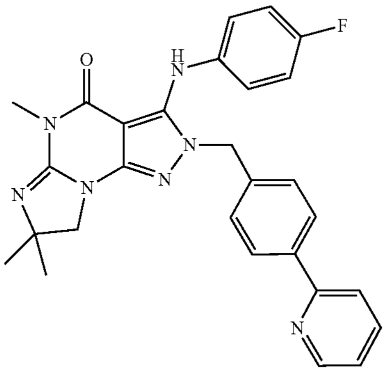

in free or pharmaceutically acceptable salt form.

8. The method according to claim 6, wherein the checkpoint inhibitor is an inhibitor of CTLA-4, PD-1 and/or PD-L1.

9. The method according to claim 6, wherein the checkpoint inhibitor is selected from nivolumab, pembrolizumab, cemiplimab, ipilimumab, avelumab, durvalumab, atezolizumab, spartalizumab, or combinations thereof.

10. The method according to claim 6, wherein the PDE1 inhibitor is administered in an amount sufficient to reduce infiltration of monocytes and/or macrophages to a tumor associated microenvironment.

11. The method according to claim 6, wherein the PDE1 inhibitor and the checkpoint inhibitor are administered in amounts together sufficient to reduce infiltration of monocytes and/or macrophages to a tumor associated microenvironment and/or to increase the infiltration of natural killer cells and CD4+ T cells.

12. The method according to claim 2, wherein the PDE1 inhibitor is selected from any of the following:

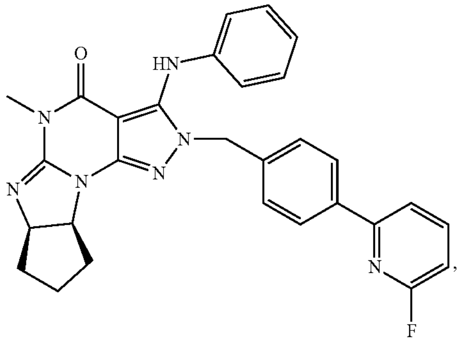

,

-continued

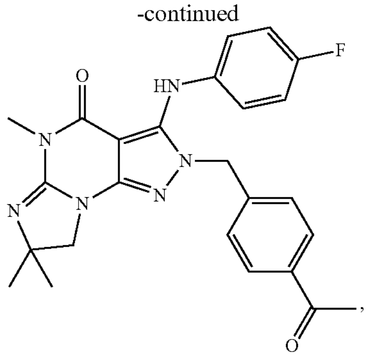

,

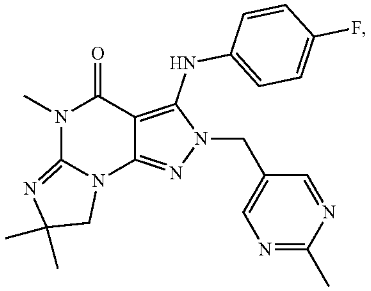

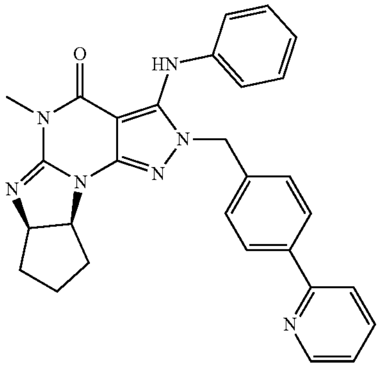

or

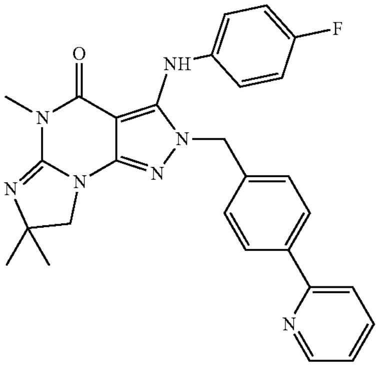

in free or pharmaceutically acceptable salt form.

* * * * *